United States Patent [19]

Debourge et al.

[11] Patent Number: 5,210,198

[45] Date of Patent: May 11, 1993

[54] FUNGICIDES CONTAINING TRIAZOLE AND OLIGOETHER GROUPS

[75] Inventors: Jean-Claude Debourge, Champagne au Mt d'Or; Alfred Greiner, Dardilly; Régis Pepin, Rillieux la Pape, all of France

[73] Assignee: Rhone-Poulenc Agrochimie, Lyons, France

[21] Appl. No.: 787,758

[22] Filed: Nov. 6, 1991

Related U.S. Application Data

[60] Continuation of Ser. No. 391,161, Aug. 8, 1989, abandoned, which is a division of Ser. No. 889,313, Jul. 23, 1986, Pat. No. 4,863,943, and a continuation-in-part of Ser. No. 693,281, Jan. 22, 1985, abandoned.

[30] Foreign Application Priority Data

Jan. 26, 1984 [FR] France .................................. 84 01424
Apr. 23, 1986 [FR] France .................................. 86 06075

[51] Int. Cl.$^5$ ............................................ C07D 405/06
[52] U.S. Cl. .............................. 548/268.8; 548/267.2; 548/267.8; 548/268.6
[58] Field of Search .................... 514/383; 548/267.2, 548/267.8, 268.6, 268.8

[56] References Cited

U.S. PATENT DOCUMENTS

| | | | |
|---|---|---|---|
| 4,255,434 | 3/1981 | Kramer et al. | 548/262 |
| 4,518,415 | 5/1985 | Marchington et al. | 514/383 |
| 4,636,247 | 1/1987 | Clough et al. | 548/262 |
| 4,863,943 | 9/1989 | DeBourge et al. | 514/383 |

OTHER PUBLICATIONS

Burger, "Medicinal Chemistry", 2nd Ed., N.Y., 1960, p. 1055.

Primary Examiner—Patricia L. Morris
Attorney, Agent, or Firm—Scully, Scott, Murphy & Presser

[57] ABSTRACT

Fungicides, which can be used especially against diseases of cereals, of formula:

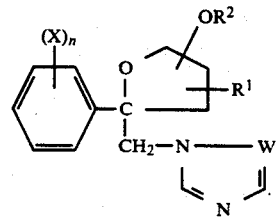

in which:
x is a halogen atom or a cyano or nitro group or an alkyl or alkoxy group, optionally halogenated,
n is a positive integer, or 0, less than 6,
W denotes a trivalent group consisting of either a =CH— group or a nitrogen atom =N—,
$R^1$ denotes a hydrogen atom or an alkyl radical,
$R^2$ denotes a hydrogen atom or an optionally substituted hydrocarbon radical.

1 Claim, No Drawings

FUNGICIDES CONTAINING TRIAZOLE AND OLIGOETHER GROUPS

This application is a continuation of Ser. No. 391,161, filed Aug. 8, 1989 and now abandoned which is a division of Ser. No. 889,313 filed Jul. 23, 1986 and now U.S. Pat. No. 4,863,943, which is a continuation-in-part of Ser. No. 693,281 filed Jan. 22, 1985 and now abandoned.

The invention relates to new compounds for use in plant protection containing triazole or imidazole groups and oligoether groups. The invention further relates to processes for preparing said compounds and products as well as their application for the protection of plants, especially in the field of controlling parasitic fungi, but also in the regulation of plant growth.

Many products containing a triazole group, especially fungicides, are already known. An object of the invention is to provide new products which make possible new ways of treating plants. Another object of the invention is to provide products which are highly active especially against rust and mildew, and more particularly against cereal mildew. Another object of the invention is to provide products which have polyvalent activity covering, in particular, grey mould (Botrytis), Leaf spot, eyespot and diseases of seeds. Further objects and advantages of the invention will become clear during the description which follows.

It has now been found that these objects could be attained by means of the products of the invention. These products are of the formula

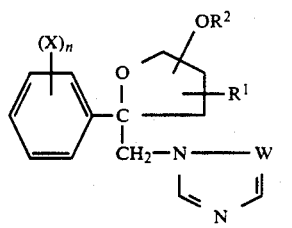

in which:
- X is a halogen atom, preferably fluorine, bromine or chlorine, or a cyano, nitro, alkyl or alkoxy group having from 1 to 12 carbon atoms, preferably from 1 to 4 carbon atoms, and optionally being mono- or polyhalogenated (especially the group $CF_3$),
- n is a positive integer, or 0, less than 6 and preferably equal to 2, on the condition that when n is greater than 1, the substituents X can be either identical or different,
- W denotes a trivalent group consisting of either a =CH— group or a nitrogen atom =N—,
- $R^1$ denotes a hydrogen atom or an alkyl radical preferably having from 1 to 4 carbon atoms,
- $R^2$ denotes a hydrogen atom or an optionally substituted hydrocarbon radical; as radicals which can more especially be used, there may be mentioned alkyl, cycloalkyl, aryl and aralkyl radicals; as substituents, there may be mentioned in particular halogen atoms, preferably chlorine and fluorine, and alkoxy and aryloxy groups. The group $OR^2$ is preferably attached to the carbon atom adjacent to the oxygen atom of the heterocycle in formula (I), so that the compound of formula (I) is then provided with an acetal function.

Among the compounds of the formula (I), the compounds in which W denotes a nitrogen atom are preferred for fungicidal applications.

I.

This subclass of products according to the invention hence consists of the products of the formula

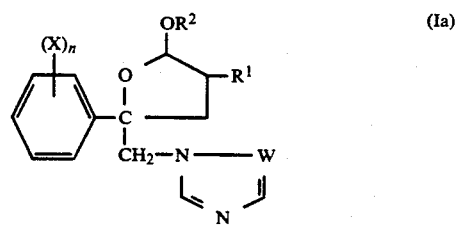

in which:
- X is a halogen atom,
- n is equal to 1, 2 or 3. For the purpose of use against eyespot, the compounds in which n=2 are preferred.

The compounds according to the invention can exist in or or more forms of optical isomers, according to the number of asymmetric centers in the molecule. The invention hence relates both to these optical isomers and to their racemic mixtures and the corresponding diastereoisomers. Separation of the diastereoisomers and/or optical isomers can be accomplished according to methods known per se.

The invention also relates to the salt forms of the compounds according to the invention, and more especially the hydrochlorides, sulphates, oxalates and nitrates.

The present invention also relates to processes for preparing the compounds according to the invention.

According to a first process, a compound of the formula

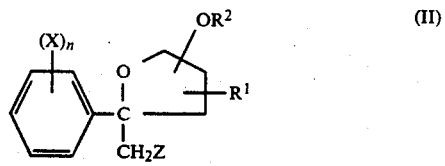

in which Z is a chlorine or bromine atom and X, n, $R^1$ and $R^2$ have the same significance as in formula (I), is reacted with an alkali metal derivative (for example, a sodium or potassium salt), or a quaternary ammonium or quaternary phosphonium derivative of an imidazole or triazole.

The reaction is usually performed in an aprotic polar solvent medium and can also be catalyzed, for example, by adding an alkali metal iodide; the temperature is generally between 50° and 250° C., preferably between 70° and 230° C. for economic reasons, overall reagent concentrations of between 1 and 50% are most frequently used.

The compounds of formula

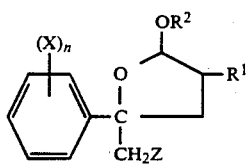 (IIa)

can be prepared by reacting an alcohol R²OH with a compound of the formula

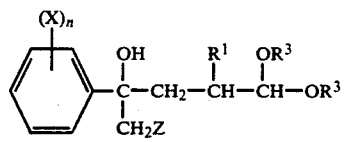 (III)

in the presence of an acidic catalyst, $R^1$, $R^2$, X, Z and n having the same significance as above, and $R^3$ being an organic radical, preferably a lower alkyl ($C_{1-4}$) radical, and two radicals $R^3$ can together form a divalent organic radical, preferably a lower alkylene radical.

The catalytic acid used in this reaction can be either a protic or an aprotic acid. As protic acids, there may be mentioned hydrochloric, sulphuric, trifluoroacetic, perchloric, benzenesulphonic, tolulenesulphonic and methanesulphonic acids. As aprotic acids, there may be mentioned Lewis acids such as $BF_3$, $AlCl_3$ and $SnCl_4$. When hydrochloric acid is used as catalyst, it may be generated in situ, for example, by means of an acyl chloride, especially acetyl chloride, which reacts with the alcohol present to give rise to HCl.

The reaction is normally performed by simply heating the reagents mentioned. The temperature is generally within the temperature range from 50° C. to the boiling point of the reaction medium. The alcohol R²OH usually performs the role of solvent in the reaction medium. An inert cosolvent can also be added, in particular, an aliphatic, alicyclic or aromatic hydrocarbon which may be halogenated or unhalogenated, or an ether.

The compounds of formula (III) are usually prepared by reacting a carbonyl compound of formula

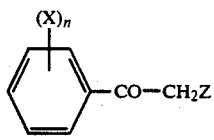 (IIIa)

with the organomagnesium derivative prepared from a compound of the formula

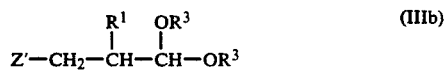 (IIIb)

in which formulae Z' is a halogen atom, preferably bromine, and X, Z, $R^1$, $R^3$ and n have the significance given above. The organomagnesium derivative can be prepared, in a manner known, per se, by the action of a β-haloaldehyde acetal on magnesium in a solvent medium. This β-haloaldehyde acetal can itself be prepared according to known methods, for example, according to G. Buchi and H. Wuest, *J. Org. Chem.*, 34, 1122 (1969)

and H. Meerwein, Houben-Weyl, *Methoden der Org. Chem.*, vol. VI/3, page 204, 4th edition (1965).

The reaction of the compound of formula (IIIa) with the organomagnesium derivative of the compound of formula (IIIb) is most frequently performed at a temperature between −70° C. and +100° C., preferably between −50° C. and +50° C. As solvent, there may be mentioned ethers, especially diethyl ether and tetrahydrofuran, or aliphatic, alicyclic or aromatic hydrocarbons, or mixtures thereof.

According to another process for preparing the compounds according to the invention, an alcohol R²OH is reacted with a compound of the formula

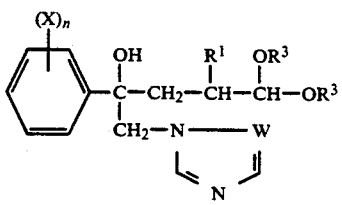 (IV)

in the presence of an acidic catalyst. The various symbols shown for the formulae of these two reagents have the significance given earlier. As acidic catalyst, those specified earlier in relation to the preparation of compounds of formula (IIa) can also be used. The other reaction conditions are also similar to those specified for the preparation of these compounds of formula (IIa).

The compounds of formula (IV) can be obtained by reacting imidazole or triazole with a compound of the formula

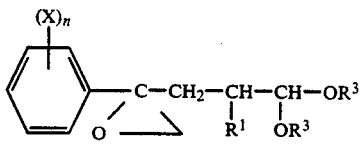 (V)

in which the various symbols have the significance already mentioned.

The imidazole or triazole is optionally completely, or preferably partially, in the form of an alkali metal salt.

The reaction is usually performed at a temperature between room temperature (20° C.) and the refluxing boiling point, preferably between +50° and +130° C. As solvents, there may be used, in particular, alcohols, ethers and aprotic polar solvents such as dimethylformamide and dimethyl sulphoxide.

Under conditions similar to those described for the preparation of compounds of formula (IV) from compounds of formula (V), these compounds of formula (IV) can also be prepared from compounds of formula (III) with the aid of an alkali methal derivative of imidazole or triazole.

The compounds of formula (V) can be obtained by dehydrohalogenation of compounds of formula (III). This reaction is usually performed by the action of an organic or, preferably, inorganic base at a temperature between 0° and 100° C. The medium can be aqueous and/or contain a solvent such as a hydrocarbon or an ether, an alcohol or a polar solvent.

The examples which follow, which are given without implied limitation, illustrate the invention and show how it can be used.

Examples 1 to 3 and Table (I) illustrate particular methods of preparing compounds according to the invention, as well as these compounds themselves. Among the physical properties given for these compounds, the values of the NMR shifts (delta) of the proton in the —O—CH—O— (acetal) group have been given. These shifts are measured in ppm and they are read with respect to a reference product, tetramethylsilane. The NMR is performed at 100 MHz in deuterated chloroform.

Examples 4 to 7 illustrate the fungicidal properties of the compounds according to the invention, as well as their applications.

In these examples, the spraying of solutions or suspensions of active substance is performed under conditions such that the spraying of a solution or suspension of concentration equal to 1 g/l corresponds on average to the application of approximately 2 microgrammes of active substance per cm² of plant leaf.

Under the conditions of Examples 4 to 7, the compounds illustrated did not show phytotoxicity.

In these examples, a product is regarded as providing complete protection against a fungal disease when the protection is at least 95%; the protection is regarded as good when it is at least 80% (but less than 95%), as fairly good when it is at least 70% (but less than 80%) and as average when it is at least 50% (but less than 70%).

In the present account, the percentages are, except where otherwise stated and except in regard to yields, percentages by weight. In the case of percentages expressed relative to the stoichiometry, these are mole percentages. As regards concentrations, some of these are expressed in ppm (part per million) which corresponds to mg/l.

EXAMPLE 1

An organomagnesium derivative is prepared by activation of magnesium (9.7 g; 0.4 mole) with dibromoethane (0.5 ml) in anhydrous tetrahydrofuran (10 ml) (abbreviated THF). While the temperature is maintained below 15° C., a solution of 2-(-bromoethyl)-1,3-dioxolane (47 ml; 0.4 mole) in THF (200 ml) is added dropwise. A quarter of an hour after the addition is completed, the mixture is cooled to −45° C. and a solution of chloromethyl para-chlorophenyl ketone (56.7 g; 0.3 mole) in THF (150 ml) is added, the temperature being maintained at −45° C. After half an hour, the mixture is neutralized by means of pure acetic acid (120 ml), and then poured into water (one liter). Extraction is performed using ethyl acetate. The solution in ethyl acetate is dried and the solvent evaporated. A chlorohydrin (100 g) is obtained, m.p. 99° C. (after recrystallization in cyclohexane), of the formula

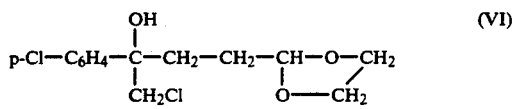

A mixture of acetylchloride (0.1 ml) and a solution of the product of formula (VI) (6 g; 0.02 mole) in methanol (30 ml) is heated to boil under reflux for 2 hours. The reaction mixture is then poured into an aqueous solution containing 5% by weight of sodium carbonate in water. The mixture is extracted with ethyl ether, the ethereal solution dired and the ether evaporated. An oil is obtained which is distilled at 140° C. under an absolute pressure of 0.04 mm Hg, and an oily product (4.7 g) is obtained of the formula

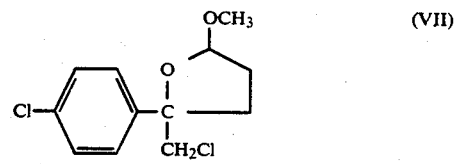

A mixture obtained by adding the product of formula (VII) (4.2 g; 0.016 mole) to dimethyl sulphoxide (40 ml) containing triazole sodium salt, prepared from triazole (1.6 g; 0.024 mole) and sodium hydride (0.7 g; 0.024 mole) in 80% strength oily suspension, is heated for 3 hours at 170° C. under an inert atmosphere.

The solution is poured into water (200 ml). The mixture is extracted with ethyl ether, the ethereal solution dried and the ether evaporated. The residue is purified by chromatography on a silica column. An oil (3.1 g) is thereby obtained which consists of a mixture in substantially equal proportions of two diastereoisomers of the structural formula

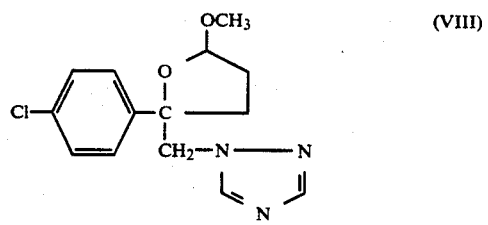

EXAMPLE 2

The product of the formula

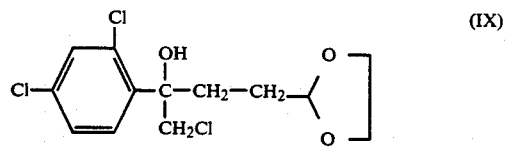

is prepared by a process similar to that for preparing the product of formula (VI) in Example 1, but using chloromethyl ortho, para-dichlorophenyl ketone as reagent in place of chloromethyl parachlorophenyl ketone.

A mixture of the product of formula (IX) (0.3 mole) with aqueous sodium hydroxide solution at 15% concentration by weight (400 ml) is stirred for 12 h at room temperature. The organic phase is diluted with ethyl ether, separated by decantation, washed with water, dried and evaporated.

On distillation, a colorless viscous oil (64 g) is obtained of b.p. 147° to 150° C. under an absolute pressure reduced to 0.02 mm Hg, which has the formula

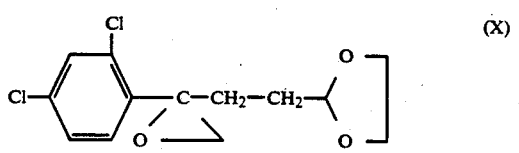

A mixture of the following is heated for 6 hours at 110° C.:

a solution of the product of formula (X) (5.8 g; 0.02 mole) in n-butanol (20 ml),
triazole (1.4 g; 0.02 mole),
triazole sodium salt (0.09 g; 0.01 mole).

The mixture is cooled to room temperature, diluted with water and extracted with ether, and the ethereal solution is then concentrated. The residue is purified by chromatography on a silica column, using as eluent a methanol/ethyl acetate/hexane mixture containing the respective proportions 5:47.5:47.5 by volume.

A product (5.1 g) is obtained of m.p. 131° C., which has the formula

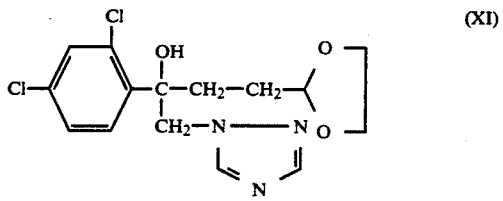

A mixture of acetyl chloride (0.10 ml) with a solution of the product of formula (XI) (3.1 g) in absolute ethanol (30 ml) is heated to boil under reflux for 4 h. The mixture is allowed to cool. The crystals formed are filtered off and washed with cold ethanol. White crystals (1.2 g) are thereby obtained, m.p. 162° C., which correspond to the more polar diastereoisomer (observed in thin layer chromatography) of the product of the structural formula

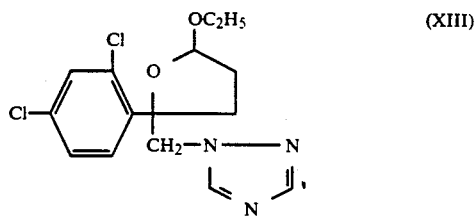

The mother liquors from this filtration are concentrated, the residue is diluted with ethanol (1 ml) and then isopropyl ether (2 ml), and the crystals formed are separated. A further 0.2 g of the same diastereoisomer is obtained, m.p. 164° C.

By chromatography on silica of the residual oil from the crystallization, a second diastereoisomer, the less polar, is obtained, m.p. 61° C.

EXAMPLE 3

Using processes similar both to that of Example 1 and those of Examples 2 and 9, various compounds were prepared which had the formula

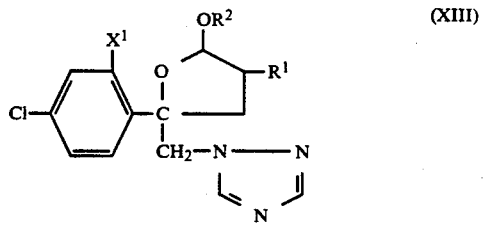

The nature of the substituents in this formula (XIII) and some physical characteristics of the compounds 1 to 50 are shown in Table (I), which also includes the products prepared (Nos. 1, 10, 11 and 29) in Examples 1, 2 and 9.

However, as regards the compound Nos. 49 and 50, instead of containing a para-chlorophenyl group substituted with $X^1$ in the ortho position, they contain a para-fluorophenyl group substituted with $X^1$ in the ortho position. Furthermore, compound No. 50 has an imidazole group instead of a triazole group, the preparation process remaining the same but the reactants been chosen appropriately.

In the case where $R^1$ is a hydrogen atom, the compounds contain 2 asymmetric carbon atoms, and the two diastereoisomers can be distinguished by thin layer chromatography on silica, using as eluent a methanol/ethyl acetate hexane mixture containing the respective proportions 5:20:75 by volume. The less polar diastereoisomer migrates faster in chromatography and is referred to as A. The more polar migrates more slowly in chromatography and is referred to as B.

In the case where $R^1$ is other than a hydrogen atom, the compounds contain 3 asymmetric carbon atoms and there are 4 diastereoisomers. These diastereoisomers are arbitrarily called A, B, C and D. They are sometimes difficult to separate by chromatography, but when this is possible, A is the least polar, D the most polar, and B and C have intermediate polarities.

EXAMPLE 4

Test in vivo on *Erysiphe graminis* on barley (barley mildew)

By fine grinding, there is prepared an aqueous emulsion of the active substance to be tested, having the following composition:
active substance to be tested 40 mg
Tween 80 (surfactant consisting of an oleate of a polycondensate of ethyleneoxide with a sorbitan derivative) diluted to 10% in water 0.4 ml
water 40 ml This aqueous emulsion is then diluted with water to obtain the desired concentration.

Barley, sown in pots in loam, is treated at the stage where it is 10 cm in height by spraying it with an aqueous emulsion (referred to as spray mixture) at the concentration stated below. The trial is repeated twice. After 48 hours, the barley plants are dusted with *Erysiphe graminis* spores, the dusting being accomplished with the aid of diseased plants.

Readings are taken 8 to 12 days after contamination.
Under these conditions, the following results are observed: At a dose of 1 g/l, good or complete protection with the compounds 1, 2, 4, 5, 6, 7, 8, 17, 18, 19, 20. At a dose of 0.33 g/l, complete protection with the compounds 8, 14, 16, 27. At a dose of 0.11 g/l, complete protection with the compounds 11, 12, 13, 15, 28. At a dose of 0.033 g/l, complete protection with the compounds 9 and 10.

EXAMPLE 5

Test in vivo on "*Puccinia Recondita*" Responsible for Wheat Rust

Wheat, sown in pots in loam, is treated at the stage where it is 10 cm in height by spraying it with aqueous emulsions (referred to as spray mixtures) of the same composition as that described in Example 4, and at various concentrations of the compound to be tested. The trial is repeated twice with each concentration.

After 48 hours, an aqueous suspension of spores (50,000 sp/cc) is sprayed onto the wheat; this suspension has been obtained from contaminated plants. The wheat is then placed for 48 hours in an incubation cell at approximately 18° C. and 100% relative humidity.

After these 2 days, the relative humidity is lowered to 60%. The condition of the plants is verified between the 11th and 15th day after contamination by comparison with the untreated control.

Under these conditions, the following results are observed: At a dose of 1 g/l, good protection with the compounds 4, 5, 6, 7, 9, 13, 14, 15, 16, 17, 18 and 21. At a dose of 0.33 g/l complete protection with the compounds 10 and 11.

EXAMPLE 6

Test on *Botrytis cinerea* on Tomato

Greenhouse-cultivated tomatoes (Marmande variety) from 30 to 40 days old are treated by spraying with aqueous emulsions (referred to as spray mixtures) of the same composition as that described in Example 4 and at various concentrations of the compound to be tested. The trial is repeated twice with each concentration.

After 24 or 48 hours, the leaves are cut and placed into 2 Petri dishes (diameter 11 cm), the base of which has been previously provided with a disc of damp filter paper (5 leaflets per dish).

The innoculum is then applied with the aid of a syringe by depositing drops (3 drops per leaflet) of a spore suspension. This suspension of spores of *Botrytis cinerea* has been obtained from a 15-day culture which has been suspended in a nutrient solution (80,000 units/cc).

Verification is carried out 3 days after contamination by comparison with an untreated control.

Under these conditions, good or complete protection is observed at a dose of 1 g/l with compound Nos. 8, 10 and 16.

EXAMPLE 7

Test in vitro on Seed Fungi and Soil Fungi

The action of the compounds according to the invention is studied on the following fungi responsible for secondary diseases of cereals:

| | |
|---|---|
| *Cercosporella herptrichoides* | (CERC) |
| *Helminthosporium gramineum* | (HELM G) |
| *Pyrenophorae avenae* | (PYRE) |
| *Septoria nodorum* | (SEPT N) |
| *Helminthosporium teres* | (HELM T) |
| *Fusarium roseum* | (FUS ROS) |
| *Fusarium nivale* | (FUS NIV) |
| *Fusarium culmorum* | (FUS CULM) |
| *Rhizoctonia cerealis* | (RHIZ C) |

The designations given in parenthesis will be used to denote these fungi in Table (II).

For each trial, the procedure is as follows: a nutrient medium consisting of potato, glucose and agar (PDA medium) is introduced supercooled into a series of Petri dishes (20 ml per dish) after sterilization in the autoclave at 120° C.

As the dishes are being filled, an acetone solution of the active substance is injected into the supercooled medium to obtain the desired final concentration.

As a control, Petri dishes similar to the above are taken in which there are poured similar amounts of a nutrient medium not containing active substance.

After 24 or 48 h, each dish is seeded by depositing a fragment of mycelium originating from a previous culture of the same fungus.

The dishes are kept for 2 to 10 days (according to the fungus tested) at 22° C., and the growth of the fungus in the dishes containing the active substance to be tested is compared with that of the same fungus in the dish used as control.

For each compound tested, the weakest dose is thus determined which enables development of the fungus in question to be 80–100% inhibited. This dose is referred to as the "minimal inhibitory dose".

These minimal inhibitory doses, expressed in ppm, are recorded in Table (II), in which the abbreviations have the significance given above.

The compounds according to the invention can thus be used for both preventive and curative control of fungi, especially of the type basidomycetes, ascomycetes, adelomycetes or fungi imperfecti, in particular, rusts, mildews, eyespot, fusarioses, helminthosporioses, septorioses and rhizoctones of vegetables and plants in general and, in particular, of cereals such as wheat, barley rye, oats and their hybrids, and also rice and maize.

The products of the invention are particularly valuable by virtue of their broad spectrum in regard to diseases of cereals (mildew, rust, eyespot, helminthosporioses, septorioses and especially the fusarioses which are difficult to control). They are also very valuable by reason of their activity towards grey mould (Botrytis) and the cercosporioses and, for this reason, they can be applied to crops as varied as vine, market-gardening crops and arboriculture.

Finally, they show excellent selectivity towards crops.

They are advantageously applied at doses from 0.02 to 5 kg/ha, preferably from 0.05 and more specifically 0.1 to 2 kg/ha.

To use them in practice, the compounds according to the invention are rarely used alone. They most frequently form part of compositions. These compositions, which can be used for the protection of plants against fungal diseases, or in compositions for regulating plant growth, contain as an active substance a compound according to the invention, as described above, in combination with solid or liquid supports which are acceptable in agriculture, and surfactants which are also acceptable in agriculture. The usual inert supports and usual surfactants can, in particular, be used.

These compositions can also contain any other type of ingredient, e.g., protective colloids, adhesives, thickeners, thixotropic agents, penetrants, stabilizers, sequestering agents and the like, as well as other known active substances having pesticidal properties (especially insecticidal or fungicidal properties) or properties which encourage plant growth (especially fertilizers) or properties of regulating plant growth. More generally, the compounds according to the invention can be combined with all the solid or liquid additives which correspond to the customary techniques of formulation.

These doses for use, in the case of using the compounds according to the invention as fungicides, can vary within broad limits, especially according to the virulence of the fungi and the climatic conditions.

Compositions containing 0.5 to 5,000 ppm of active substance are generally very suitable; these values apply to the compositions ready for application. Ppm means "parts per million". The range from 0.5 to 5,000 ppm is equivalent to a range from $5 \times 10^{-5}$ to 0.5% (percentages by weight).

As regards compositions intended for storage and transportation, these more advantageously contain from 0.5 to 95% (by weight) of active substance.

Thus, the compositions for agricultural use according to the invention can hence contain the active substances according to the invention within very broad limits, ranging from $5 \times 10^{-5}$% to 95% (by weight).

According to what has already been stated, the compounds according to the invention are generally mixed with supports and optionally with surfactants.

In the present account, the term "support" denotes an organic or inorganic, natural or synthetic material which is in combination with the active substance to facilitate the application of the latter to the plant, the seeds or the soil. This support is hence generally inert, and it must be acceptable in agriculture, especially on the plant treated. The support can be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquified gases, and the like).

The surfactant can be an emulsifier, dispersant or wetting agent of ionic or nonionic type. There may be mentioned, e.g., salts of polyacrylic acids, salts of lignosulphonic acids, salts of phenolsulphonic or naphthalenesulphonic acids, polycondensates of ethylene oxide with fatty alcohols or fatty acids or fatty amines, substituted phenols (especially alkylphenols or arylphenols), salts of sulphosuccinic acid esters, taurine derivatives (especially alkyltaurates) and phsphoric acid esters of polycondensates of ethylene oxide with alcohols or phenols. The presence of at least one sufractant is generally essential when the active substance and/or the inert support are not water-soluble and the vector agent for the application is water.

For their application, the compounds of formula (I) are generally in the form of compositions; these compositions according to the invention are themselves in fairly diverse solid or liquid forms.

As solid forms of compositions, there may be mentioned powders for dusting or scattering (with a content of the compound of formula (I) ranging up to 100%) and pellets, especially those obtained by extrusion, by compacting, by impregnation of a granulated support, or by granulation starting from a powder (the content of the compound of formula (I) in these pellets being between 1 and 80% in the latter cases).

As liquid forms of compositions, or forms designed to constitute liquid compositions when applied, there may be mentioned solutions, especially the water-soluble concentrates, emulsifiable concentrates, emulsions, flowables, aerosols, wettable powders (or powder for spraying) and pastes.

The emulsifiable or soluble concentrates most frequently contain 10 to 80% of active substance, whereas the emulsions or solutions ready for application contain 0.01 to 20% of active substance. In addition to the solvent, the emulsifiable concentrates can contain, when necessary, 2 to 20% of suitable additives such as stabilizers, surfactants, penetrants, corrosion inhibitors, colorings and adhesives. By way of example, the composition of a few concentrates is as follows:

Example F (formulation) 1:

| | |
|---|---|
| active substance | 400 g/l |
| alkali metal dodecylbenzenesulphonate | 24 g/l |
| 10:1 ethylene oxide/nonylphenol condensate | 16 g/l |
| cyclohexanone | 200 g/l |
| aromatic solvent | q.s. 1 liter |
| According to another formula for an emulsifiable concentrate, there are used: | |
| Example F2: | |
| active substance | 250 g |
| epoxide-treated vegetable oil | 25 g |
| mixture of alkylaryl sulphonate, polyglycol ether and fatty alcohols | 100 g |
| dimethylformamide | 50 g |
| xylene | 575 g |

From these concentrates, by dilution with water, it is possible to obtain emulsions of any desired concentration, which are especially suitable for application to leaves.

Flowables, which can also be applied by spraying, are prepared so as to obtain a stable fluid product which does not settle, and they usually contain from 10 to 75% of active substance, from 0.5 to 15% of surfactants, from 0.1 to 10% of thixotropic agents, from 0 to 10% of suitable additives such as antifoams, corrosion inhibitors, stabilizers, penetrants and adhesives and, as a support, water or an organic liquid in which the active substance is of low solubility or insoluble: some solid organic substances or inorganic salts can be dissolved in the support to assist in preventing sedimentation, or as antifreeze for the water.

The wettable powders (or powder for spraying) are usually prepared so as to contain 20 to 95% of active substance, and they usually contain, in addition to the solid support, from 0 to 5% of a wetting agent, from 3 to 10% of a dispersant and, when necessary, from 0 to 10% of one or more stabilizers and/or other additives such as penetrants, adhesives, or anti-caking agents, colorings, and the like.

By way of example, various compositions of wettable powders are as follows:

| Examples F3: | |
|---|---|
| active substance | 50% |
| calcium lignosulphonate (deflocculant) | 5% |
| isopropyl naphthalenesulphonate (anionic wetting agent) | 1% |
| anti-caking silica | 5% |
| kaolin (filler) | 39% |
| Another composition of powder for spraying, at 70% strength, uses the following constituents: | |
| Example F4: | |
| active substance | 700 g |
| sodium dibutylnaphthalenesulphonate | 50 g |
| condensation product of naphthalenesulphonic acid, phenolsulphonic acid and formaldehyde in proportions 3:2:1 | 30 g |
| kaolin | 100 g |
| whitening | 120 g |
| Another composition of powder for spraying, at 40% strength, uses the following constituents: | |
| Example F5: | |
| active substance | 400 g |
| sodium lignosulphonate | 50 g |
| sodium dibutylnaphthalene sulphonate | 10 g |
| silica | 540 g |

Another composition of powder for spraying, at 25% strength, uses the following constituents:

| Example F6: | |
|---|---|
| active substance | 250 g |
| calcium lignosulphonate | 45 g |
| mixture of whitening and hydroxyethyl cellulose in equal parts by weight | 19 g |
| sodium dibutylnaphthalenesulphonate | 15 g |
| silica | 195 g |
| whitening | 195 g |
| kaolin | 281 g |

Another composition of powder for spraying, at 25% strength, uses the following constituents:

| Example F7: | |
|---|---|
| active substance | 250 g |
| isooctylphenoxy-polyoxyethylene-ethanol | 25 g |
| mixture of whitening and hydroxyethyl cellulose in equal parts by weight | 17 g |
| sodium aluminosilicate | 543 g |
| kieselguhr | 165 g |

Another composition of powder for spraying, at 10% strength, uses the following constituents:

| Example F8: | |
|---|---|
| active material | 100 g |
| mixture of sodium salts of sulphates of saturated fatty acids | 30 g |
| condensation product of naphthalenesulphonic acid and formaldehyde | 50 g |
| kaolin | 820 g |

To obtain these powders for spraying or wettable powders, the active substances are intimately mixed in suitable mixers with the additional substances, and the mixtures are ground in suitable mills or other grinders. Powers for spraying are thereby obtained, the wettability and suspendability of which are advantageous; they can be suspended in water at any desired concentration and these suspensions can be very advantageously used, especially for application to plant leaves.

Instead of wettable powders, pastes can be produced. The conditions are methods of production and use of these pastes are similar to those for wettable powders or powders for spraying.

As already stated, the dispersions and aqueous emulsions, e.g., the compositions obtained by diluting with water a wettable powder or an emulsifiable concentrate according to the invention, are included within the general scope of the present invention. The emulsions can be of the water-in-oil or oil-in-water type, and they can have a thick consistency like that of "mayonnaise".

Pellets intended for placing on the soil are usually prepared so as to be between 0.1 and 2 mm in size, and they can be manufactured by agglomeration or impregnation. In general, the pellets contain 0.5 to 25% of active substance and 0 to 10% of additives such as stabilizers, slow release modification agents, binders and solvents.

According to an example of a pellet composition, the following constituents are used:

| Example F9: | |
|---|---|
| active substance | 50 g |
| epichlorohydrin | 2.5 g |
| cetyl polyglycol ether | 2.5 g |
| polyethylene glycol | 35 g |
| kaolin (particle size: 0.3 to 0.8 mm) | 910 g |

In this particular case, the active substance is mixed with the epichlorohydrin and dissolved in 60 g of acetone; the polyethylene glycol and cetyl polyglycol ether are then added. The kaolin is wetted with the solution obtained and the acetone is then evaporated under vacuum. Such a micropellet is advantageously used to control soil fungi.

The compounds of formula (I) can further be used in the form of powders for dusting; a composition comprising 50 g of active substance and 950 g of talc can also be used; a composition comprising 20 g of active substance, 10 g of finely divided silica and 970 g of talc can also be used; these constituents are mixed and ground, and the mixture is applied by dusting.

Further examples were also made. In these examples, the following abbreviations have been used:

| | |
|---|---|
| Botrytis cinerea | BOT |
| Erysiphe graminis | ERYG |
| Puccinia recondita | PUCR |
| Plasmopara viticola | PLA |
| Piricularia oryzae | PIR |
| Cercospora beticola | CBET |
| Peronospora tabacina | PERO |
| Puccinia striiformis | PUCS |
| Erysiphe cichoracearum | ERYC |
| Fusarium oxysporum (meloni) | FUS OX |
| Pythium spp | PTY |
| Pyrenopnora avenae | PYR |
| Septoria tritici | SEPT T |
| Venturia inequalis | VENT |
| Whetzelinia schlerotiorum | WHE |
| Monilia laxa | MON |
| Mycosphaerella fijiensis | MSPH |
| Marssonina panattoniana | MARS |
| Alternaria solani | ALT |
| Aspergillus niger | ASP |
| Cercospora arachidicola | CARA |
| Cladosporium herbarum | CLAD |
| Helminthosporium oryzae | HELM OR |
| Penicillium expansum | PEN |
| Pestalozzia sp | PES |
| Phialophora cinerescens | PHI |
| Phoma betae | PHB |
| Phoma foveata | PHF |
| Phoma lingam | PHL |
| Ustilago maycis | USI |
| Verticillium dahliae | VERT |
| Ascochyta pisi | ASCO |
| Guignardia bidwellii | GUIG |
| Corticium rolfsii | CRO |
| Phomopsis viticola | PHV |
| Sclerotinia sclerotiorum | SCL S |
| Sclerotinia mino | SCL M |
| Phytophthora cinnamomi | PHY CI |
| Phytophthora cactorum | PHY CC |
| Phytophthora capsici | PHY CP |
| Phytophthora infestans | PHY IN |
| Phytophthora parasitica | PHY PA |
| Phytophthora megasperma | PHY ME |
| Phytophthora syringae | PHY SY |
| Coryneum cardinale | CORY |
| Rhizoctonia solani | RHIZ S |

The symbol > signifies "greater than" The symbol ≦ signifies "less than or equal to" Eyespot is designated Cercosporella herpotrichoides, above, but it is normally called Pseudocercosporella herpotrichoides.

Tables (III), (IV) and (VI) show the minimal inhibitory dose in vitro of various compounds in respect of various fungii according to the method of application used in the example.

Table (V) shows the minimal inhibitory dose under glass (in vivo) of various compounds in respect of various fungii according to the methods of application used in Examples 4 to 6.

Table (VII) shows the efficacy of the products in the open field as regards various compounds.

The nature of the test used under glass (in vivo) as regards Cercospora beticola (Example 8) and the conditions of the open field tests (Example 8a) are given below.

EXAMPLE 8

Sugar-beet plantlets 7 to 10 cm tall are treated preventively with the spray mixture to be tested, this spray mixture being similar to that described in Example 4. The trial is repeated twice at each concentration.

24 Hours after treatment, the beet plantlets are contaminated by spraying them with an aqueous suspension of 0.2 g/ml of mycelium of *Cercospora beticola*.

Incubation is allowed to continue for 72 h at 25° C. and 100% relative humidity, and after 3 days the plantlets are then placed in the light (10,000 lux; 14 hours per day). Verification of the condition of the plants is carried out 14 days after contamination, and is expressed as a percentage relative to an untreated control. An identical effect in the control is noted as 0%. Complete protection of the plant is noted as 100%.

EXAMPLE 8a

The particular conditions of the various tests are given in the Table (VII). The general conditions are as follows: the tests were repeated 4 times each, on plots of land from 3 to 5 m² in area. Contamination is natural for mildew (ERYG), and artificial for eyespot (CERC) and yellow rust (PUCR). The plants were treated with a spray mixture, spread in the proportion of 500 to 1,000 l/ha under a pressure of 3 kg/cm².

The treatment was preventive for mildew and yellow rust (treatment repeated every 15 days), and curative for eyespot. The results were observed on a sample of 25 leaves for mildew and yellow rust (determination of the percentage of leaf surface attacked by the disease), or on a sample of 25 stems for eyespot (determination of the percentage of stems attacked).

EXAMPLE 9

A solution of methacrolein (296 g; 4.23 moles) in dichloromethane (1 l) is cooled to 0° C. Gaseous HBr (343 g) is bubbled in while the temperature is maintained. After ¼ hour, methanol (0.9 l) is added at 0° C., at which temperature the mixture is maintained for 3 h. Water (2 l) containing concentrated (aqueous) ammonia solution (100 ml) is added. The mixture is decanted, the organic phase separated and the aqueous phase extracted with dichloromethane (200 ml). The organic phases are combined and washed with aqueous sodium bisulphite solution; the mixture is concentrated and then distilled in the presence of diethylaniline. The bromoacetal (452 g) of formula Br—CH$_2$—CH(CH$_3$)—CH(OCH$_3$)$_2$ is obtained. Yield: 54%; b.p. 44° to 50° under reduced pressure of 4 mm Hg.

A magnesium derivative is then prepared by adding a solution of bromoacetal (19.7 g) in tetrahydrofuran (40 ml) dropwise to magnesium at between 15 and 22° C. and in the presence of 1,2-dibromoethane (a few drops).

Tetrahydrofuran (40 ml) is then added, the mixture is cooled to −20° C. and a solution of trichloroacetophenone (20.1 g) in THF (50 ml) is then added dropwise. The temperature is still maintained at −20° C. Acetic acid (6 ml) is added and the mixture is poured into water (500 ml) at room temperature. The mixture is extracted with ether; the organic solution is dried and concentrated so as to obtain a yellow oil (30 g) consisting chiefly of the chlorohydrin of the formula

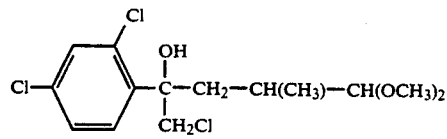

(This procedure for preparing a non-cyclic acetal is that which can give rise to compounds of Example 3 in which R$^1$ is other than a hydrogen atom.)

Into a solution of chlorohydrin (442 g) in ethanol (1.5 l), there is poured a solution of KOH (1 mole) in methanol (200 ml) until the medium becomes basic. The mixture is concentrated under vacuum, diluted with ether, washed with water, dried over sodium sulphate, evaporated and distilled under reduced pressure (121° to 140° C. under 0.01 mm Hg). There is obtained a mixture (138 g) of two diastereoisomers of the general formula

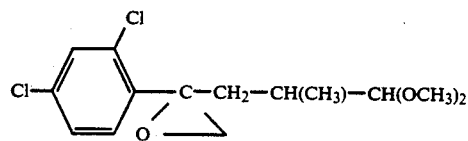

To a solution of this epoxide (126.5 g) in dimethyl formamide (500 ml) there is added triazole (57.2 g) and then K$_2$CO$_3$ (172 g). The mixture is heated to 120° C. for 4 hours, filtered, washed with dimethyl formamide and evaporated. The residue is poured into water (2 l), extracted with CHCl$_3$, washed with water, dried over Na$_2$SO$_4$ and evaporated under vacuum. A pale brown oil (148.2 g) is obtained which is triturated in heptane (100 ml). The mixture is filtered and a beige powder (117.5 g), m.p. 117° C., is obtained (yield: 78%) which consists of a mixture of the two diastereoisomers of the formula

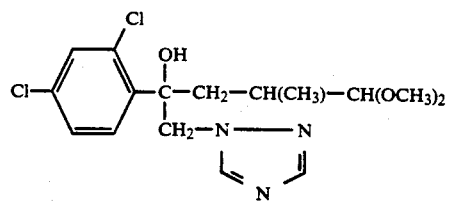

The NMR shifts delta) at 100 megahertz in deuterated chloroform are read for the protons of the methoxy group. Shifts at 3.23 and 3.19 ppm are observed for one diastereoisomer, and at 3.38 and 3.20 ppm for the other diastereoisomer.

To a solution of this hydroxytriazole (75 g) in ethanol (700 ml) there is added gaseous HCl (7.3 g), and the mixture is then heated to boil under reflux for 15 hours. The ethanol is evaporated under vacuum; the residue is taken up in ethyl acetate, washed with aqueous sodium bicarbonate solution, washed with water and dried over Na$_2$SO$_4$. The solvent is evaporated. A pale brown oil (68.6 g) is obtained. Yield 96% of product of the formula

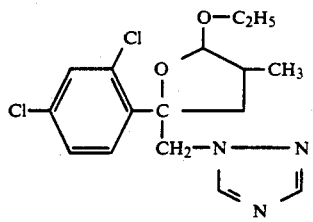

Among the product of formulae (I) and (Ia) according to the invention, the compounds are preferred in which $R^1$ is $R_4$, the $R^4$ radical being an alkyl radical.

These compounds form a class which has especially advantageous properties, and are a special subject of the present invention. Corresponding to these compounds, the intermediate products of formulae (II), (IIa), (III), (IIIb), (IIIc), (IV) and (V) in which $R^1$ is $R^4$ also form a class of compounds which are a subject of the present invention. Likewise, the processes by which these various compounds can be prepared, according to the routes described above, but choosing $R^4$ in place of $R^1$, are also a special subject of the invention.

Still more preferably, in these various compounds and processes, $R^4$ denotes a lower alkyl ($C_1$ to $C_4$) radical, and still more specifically, a methyl radical.

The various processes described above are applied to the various compounds of formulae (I) to (V) both when $R^1$ is a hydrogen atom and when $R^1$ is $R^4$. However, the preparation of the compound of formula (III) from reagents of formulae (IIIa) and (IIIb) differs according to whether $R^1$ is H or $R^1$ is $R^4$ when $R^1$ is a hydrogen atom, the reagent of formula (IIIb) is a reagent of formula

in which Z′ has the significance already mentioned and the two radicals $R^3$ can either be distinct (identical or different) or alternatively (and this is preferred) they can constitute a single divalent radical; when $R^1$ is $R^{10}$, the reagent of formula (IIIb) has the formula

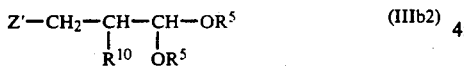

in which Z′ and $R^4$ have the significance already mentioned and the two radicals $R^5$ have the same significance as that given for $R^3$ except that the two radicals R must be distinct (and not constitute a single divalent radical). The reference H. Wuest, *J. Org. Chem.*, 34, 1122 (1969) relates to products of formula (IIIb) in which the two radicals $R^3$ constitute a single divalent radical. The reference Houben-Weyl, vol. VI/3, p. 204, 4th ed., 1965 is concerned with products of formula (IIIb2) in which the two radicals $R^5$ are distinct.

The products of formulae (I) and (Ia) in which $R^2$ is a halogenated alkyl radical, especially a chlorinated or fluorinated radical, also form a subject of the invention.

The application of the various compounds of formulae (I) and (Ia), in which $R^1$ and $R^2$ and the other substituents have the various significances mentioned above, in controlling fungal attack of cereals forms yet another subject of the invention.

In addition to the applications already described above, the products according to the invention also have excellent biocidal activity in respect of many other varieties of microorganisms, among which there may be mentioned, without implied limitation, fungii such as those of the genera:
Pullularia, e.g., the species *P. pullulas*,
Chaetomium, e.g., the species *C. globosum*,
Aspergillus, e.g., the species *Aspergillus niger*,
Coniophora, e.g., the species *C. puteana*.

As a result of their biocidal activity, the products of the invention permit effective control of the microorganisms the proliferation of which creates many problems in the agricultural and industrial fields. For this purpose, they are most especially suitable for the protection of plants or industrial products such as wood, leather, paints, paper, rope, plastics and industrial water systems. They are most especially well suited to the protection of lignocellulose products and especially timber, whether furnishing timber, structural timber or timber exposed to the elements such as fencing timber, vine stakes and railway sleepers.

In the composition of the invention, the products according to the invention used in the treatment of timber can optionally be mixed with one or more known biocidal products such as pentachlorophenol, metal salts, especially those of copper, manganese, cobalt, chromium and zinc derived from inorganic or carboxylic acids (heptanoic, octanoic and naphthenic acids), organic complexes of tin, and mercaptobenzothiazole.

Example No. 10 which follows illustrates the biocidal activity of compounds according to the invention.

EXAMPLE 10

A microsuspension of the product is prepared for determination of its fungistatic threshold. This microsuspension is prepared in the following manner: In a bead milling apparatus, each tube is charged with
- an aqueous solution (6 ml) containing two wetting agents (4% polyglycol 400 and 0.4% Tween 80)
- glass beads 3 mm in diameter (5 g)
- glass beads 5 mm in diameter (3 g)

This charge is subjected to agitation until a homogeneous microsuspension is obtained.

Specified quantities of microsuspension thus obtained are introduced into an agar-containing culture medium present in haemolysis tubes. Each medium is then seeded with a specified strain of fungus. For each culture, the amount of biocidal product is varied. The fungistatic threshold is expressed as the amount of biocidal product per 100 ml of culture medium at which an influence of the product on the development of the strain begins to be observed.

The mixtures were classified in five categories of increasing fungistatic efficacy:

| Class | |
|---|---|
| 0 | completely ineffective at $1 \times 10^{-2}$ |
| 0+ | efficacy in the region of $1 \times 10^{-2}$ |
| 1 | efficacy between $1 \times 10^{-2}$ and $1 \times 10^{-3}$ |
| 1+ | efficacy in the region of $1 \times 10^{-3}$ |
| 2 | efficacy between $1 \times 10^{-3}$ and $1 \times 10^{-4}$ |
| 2+ | efficacy in the region of $1 \times 10^{-4}$ |
| 3 | efficacy between $1 \times 10^{-4}$ and $1 \times 10^{-5}$ |
| 3+ | efficacy in the region of $1 \times 10^{-5}$ |
| 4 | efficacy between $1 \times 10^{-5}$ and $1 \times 10^{-6}$ |
| 4+ | efficacy in the region of $1 \times 10^{-6}$ |
| 5 | efficacy between $1 \times 10^{-6}$ and $1 \times 10^{-7}$ |

The fungistatic thresholds of the mixtures are determined for the following strains:
Coriolus versicolor,
Coniophora puteana,
Pullularia pullulans,
Chaetomium globosum,
Sterrigmatocystis nigra (Aspergillus niger).

The results obtained are recorded in the table which follows and are given by comparison with those obtained under the same experimental conditions with pentachlorophenol.

| Fungicidal activity on | Threshold of efficacy (Class) | |
|---|---|---|
| | Compound No. 28 | PENTACHLOROPHENOL |
| Coriolus versicolor | 4 | 3 |
| Coniophora puteana | 4+ | 3 |
| Pullularia pullulans | 4 | 3 |
| Chaetomium globosum | 3 | 3 |
| Aspergillus niger | 2+ | 3 |

The products according to the invention are hence especially advantageous for treating timber.

TABLE (I)

| Compound n° | $X^1$ | $R^1$ | $R^2$ | Diastereoisomers | Melting point | delta (NMR) |
|---|---|---|---|---|---|---|
| 1 (ex. 1) | H | H | $CH_3-$ | A + B | oil | 5,15 / 5,02 |
| 2 | H | H | $C_2H_5-$ | A | 88 | 5,27 |
| 3 | H | H | $C_2H_5-$ | B | oil | 5,14 |
| 4 | H | H | $n-C_3H_7-$ | A | oil | 5,26 |
| 5 | H | H | $n-C_3H_7-$ | B | oil | 5,12 |
| 6 | H | H | $n-C_4H_9-$ | A + B | oil | 5,25 / 5,11 |
| 7 | H | H | $iso-C_3H_7-$ | A | oil | 5,39 |
| 8 | H | H | $iso-C_3H_7-$ | B | 70 | 5,24 |
| 9 | Cl | H | $CH_3-$ | A + B | oil | 5,20 / 5,04 |
| 10 (ex. 2) | Cl | H | $C_2H_5-$ | A | 61 | 5,30 |
| 11 (ex. 2) | Cl | H | $C_2H_5-$ | B | 164 | 5,14 |
| 12 | Cl | H | $n-C_3H_7-$ | A + B | oil | 5,14 / 5,31 |
| 13 | Cl | H | $n-C_3H_7-$ | A | oil | 5,31 |
| 14 | Cl | H | $n-C_3H_7-$ | B | 116 | 5,14 |
| 15 | Cl | H | $iso-C_3H_7-$ | A | 100 | 5,42 |
| 16 | Cl | H | $iso-C_3H_7-$ | B | 149 | 5,26 |
| 17 | Cl | H | $n-C_4H_9-$ | A (85%) | oil | 5,30 |
| 18 | Cl | H | $n-C_4H_9-$ | B (90%) | oil | 5,14 |
| 19 | Cl | H | $n-C_5H_{11}-$ | A (60%) | oil | 5,30 |
| 20 | Cl | H | $n-C_5H_{11}-$ | B (90%) | oil | 5,13 |
| 21 | Cl | H | $Cl-CH_2-CH_2-$ | A | 103 | 5,35 |
| 22 | Cl | H | $Cl-CH_3-CH_2-$ | B | 135 | 5,19 |
| 23 | Cl | H | cyclohexyl | A + B | oil | 5,47 / 5,31 |
| 24 | Cl | H | cyclohexyl | B | 118 | 5,31 |
| 25 | Cl | H | $p-Cl-C_6H_4-O-CH_2-CH_2-$ | A | oil | 5,39 |
| 26 | Cl | H | $p-Cl-C_6H_4-O-CH_2-CH_2-$ | B | 128 | 5,22 |
| 27 | Cl | $CH_3$ | $n-C_4H_9-$ | A + B + C + D | oil | |
| 28 | Cl | $CH_3$ | $CH_3-$ | A + B + C + D | oil | 4,90/4,74 4,74/4,55 |
| 29 | Cl | $CH_3$ | $CH_2H_5-$ | A + B + C + D | oil | 5,01/4,64 4,82/4,62 |
| 30 | Cl | $CH_3$ | $n-C_3H_7-$ | A + B + C + D | oil | 5,01/4.83 4,81/4.60 |
| 31 | Cl | $n-C_3H_7-$ | $CH_3-$ | A + B + C + D | oil | |
| 32 | Cl | $n-C_3H_7-$ | $C_2H_5-$ | A + B + C + D | oil | |
| 33 | Cl | H | $iso-C_4H_9-$ | A | 71° | 5,29 |
| 34 | Cl | H | $iso-C_4H_9-$ | B | 80° | 5,12 |
| 35 | Cl | $CH_3$ | $n-C_3H^7$ | A + B | oil | 5,00/4,81 |
| 36 | Cl | $n-C_3H_7-$ | $C_2H_5-$ | C + D | oil | 4,83/4,61 |
| 37 | Cl | H | allyl | A | 75° C. | |
| 38 | Cl | H | allyl | B | 181° C. | |
| 39 | Cl | $CH_3$ | $F-CH_2-CH_2-$ | A + B | oil | 5,05/4,90 |
| 40 | Cl | $CH_3$ | $F-CH_2-CH_2-$ | C + D | oil | 4,91/4,66 |
| 41 | Cl | $CH_3$ | $F-CH_2-CH_2-$ | A + B + C + D | oil | 5,05/4,91 4,90/4,66 |
| 42 | Cl | $CH_3$ | $CF_3-CH_2-$ | A + B | oil | 5,09/4,95 |
| 43 | Cl | H | $F-CH_2-CH_2-$ | A | 107° | 5,29 |
| 44 | Cl | H | $F-CH_2-CH_2-$ | B | 158° | 5,14 |
| 45 | Cl | H | $C_2H_5-$ | A + B | 57° | 5,30/5,14 |
| 47 | Cl | H | H | A + B | 171° | |
| 48 | Cl | $n-C_3H_7$ | H | A + B + C + D | 152° | |
| 49 | F | H | $C_2H_5-$ | A + B | oil | 5,24 / 5,08 |
| 50 | F | H | $C_2H_5-$ | A + B | oil | 5,24 / 5,12 |

TABLE (II)

| Compound n° | CERC | HELM G | PYRE | HELM T | SEPT N | FUS ROS | FUS NIV | FUS CULM | RHIZ C |
|---|---|---|---|---|---|---|---|---|---|
| 1 |  | 100 | 100 | 100 | 100 |  |  | 100 |  |
| 2 |  | 33 |  |  | 33 |  |  | 33 |  |
| 3 |  | 100 |  |  |  |  |  |  |  |
| 4 | 100 | 100 | 100 | 100 | 100 | 100 | 33 | 33 | 100 |
| 5 | 100 |  |  |  |  |  | 100 | 100 | 100 |
| 6 | 100 | 100 | 100 | 100 | 100 | 100 | 33 | 33 | 100 |
| 7 | 100 | 100 | 100 | 100 | 100 | 100 | 33 | 33 | 100 |
| 8 | 11 | 100 |  |  |  | 33 | 33 | 33 | 100 |
| 9 | 1,1 | 11 | 3,3 | 3,3 | 3,3 | 33 | 33 | 11 | 11 |
| 10 | 3,3 | 11 | 3,3 | 1,1 | 1,1 | 11 | 11 | 11 | 1,1 |
| 11 | 3,3 | 100 | 33 | 33 | 1,1 | 100 | 100 | 33 | 33 |
| 12 | 1,1 | 33 | 11 | 1,1 | 3,3 | 33 | 33 | 33 | 11 |
| 15 | 100 | 33 | 33 | 33 | 33 | 100 | 100 | 33 | 33 |
| 16 | 11 |  |  |  | 100 | 33 | 33 | 33 | 100 |
| 17 | 1,1 |  | 11 | 3,3 | 3,3 | 33 | 33 | 33 | 11 |
| 18 | 3,3 |  | 33 | 33 | 33 | 33 | 33 | 33 | 11 |
| 19 | 3,3 |  | 11 | 11 | 11 | 33 | 33 | 33 | 11 |
| 20 | 1,1 | 100 | 33 | 33 | 100 | 33 | 100 | 33 | 11 |
| 21 | 100 | 11 | 11 | 11 | 11 | 100 | 100 | 100 | 33 |
| 22 | 100 | 100 | 100 | 100 | 100 | 100 | 100 | 100 | 100 |
| 25 |  | 100 | 100 | 100 |  |  |  |  |  |

TABLE (III)

Minimal inhibitory doses in ppm

| Fungus | compound n° | Minimal inhibitory dose |
|---|---|---|
| ALT | 29 | 30 |
| ASP | 29 | 100 |
| BOT resistant to iprodione | 29 | 10 |
| CBET | 29 | 100 |
| CARA | 29 | 3 |
| CLAD | 29 | 30 |
| FUS CULM | 29 | 30 |
| FUS OX | 29 | 100 |
| HELM OR | 29 | 100 |
| PEN | 29 | 100 |
| PES | 29 | 30 |
| PHI | 29 | 30 |
| PHB | 29 | 10 |
| PHF | 29 | 100 |
| PHL | 29 | 10 |
| PHY CI | 29 | 100 |
| PHY CC | 29 | 100 |
| PHY CP | 29 | 100 |
| PHY IN | 29 | 100 |
| PHY PA | 29 | 100 |
| PHY ME | 29 | 100 |
| PHY SY | 29 | 100 |
| SCL S | 29 | 10 |
| USI | 29 | 3 |
| VERT | 29 | 10 |
| ASCO | 29 | 30 |
| GUIG | 29 | 100 |
| CRO | 29 | 10 |
| SEPT T | 29 | 100 |
| PHV | 29 | 30 |
| SCL M | 29 | 10 |
| CORY | 29 | 30 |
| VENT | 31 | 10 |
|  | 28 | 3 |
|  | 29 | 3 |
|  | 35 | 10 |
| WHE | 29 | 10 |
|  | 31 | 30 |
|  | 28 | 10 |
|  | 35 | 10 |
| PIR | 28 | 10 |
|  | 29 | 10 |
|  | 35 | 30 |
| MON | 31 | 10 |
|  | 28 | 10 |
|  | 29 | 1 |
|  | 35 | 10 |
| MSPH | 28 | 30 |
|  | 29 | 1 |
| MARS | 28 | 10 |
|  | 29 | 10 |

TABLE (IV)

Minimal inhibitory dose in ppm

| Fungus | 28 | 29 | 30 | 31 | 32 | 33 | 34 | 35 | 36 | 37 |
|---|---|---|---|---|---|---|---|---|---|---|
| BOT | 10 | 10 | 30 | 100 |  |  |  | 10 |  | 10 |
| FUS OX | 100 | 100 | 100 | >100 | >100 | >100 | 100 | >100 | >100 | >100 |
| PYT | 100 | >100 | >100 | >100 | >100 | 100 | 100 | >100 | >100 | >100 |
| RHIZ S | 30 | 100 | 100 | 100 | 30 | 30 | 100 | 30 | 100 | 3 |
| FUS CULM | 30 | 30 | 30 | 100 | 100 | 100 | 100 | 30 | 100 | 100 |
| FUS NIV | 30 | 30 | 30 | 100 | 100 | 100 | 100 | 100 | 100 | 100 |
| FUS ROS | 30 | 100 | 100 | 100 | 100 | 100 | 100 | 30 | 30 | 100 |
| CERC | 10 | ≦1 | 10 | 100 | 30 | 30 | 100 | 10 | 30 | 10 |
| HELM G | 10 | 3 | 10 | 30 | 100 | 100 | 100 | 10 | 100 | 30 |
| PYRE | 10 | 10 | 10 | 100 | 100 | 100 | 100 | 10 | 100 | 10 |
| HELM T | 3 | 3 | 3 | 30 | 100 | 100 | 100 | 10 | 100 | 10 |
| SEPT N | 3 | ≦1 | 3 | 30 | 100 | 30 | 100 | 10 | 100 | 10 |
| RHIZ C | 30 | ≦1 | 10 | 100 | 100 | 100 | 100 | 10 | 10 | 100 |
| SEPT T | >100 |  | 100 | >100 |  | >100 |  |  |  | 100 |

| Fungus | 38 | 39 | 40 | 41 | 42 | 43 | 44 | 49 | 50 |
|---|---|---|---|---|---|---|---|---|---|

TABLE (IV)-continued

| | | | | | | | | | |
|---|---|---|---|---|---|---|---|---|---|
| BOT | | 10 | | 10 | 30 | 30 | | 100 | 100 |
| FUS OX | >100 | >100 | >100 | >100 | | | | | |
| PYT | >100 | | >100 | | | >100 | | | |
| RHIZ S | 30 | 100 | 100 | 100 | >100 | 100 | | | 100 |
| FUS CULM | 100 | 30 | 100 | 30 | 100 | 100 | 100 | 100 | 100 |
| FUS NIV | 100 | 30 | 100 | 100 | 100 | 100 | >100 | 100 | 100 |
| FUS ROS | 100 | 100 | 100 | 100 | 100 | 100 | | >100 | 100 |
| CERC | 10 | 10 | 100 | 10 | 100 | 3 | 100 | 10 | 10 |
| HELM G | 100 | 100 | 100 | 30 | 100 | 30 | >100 | 100 | 100 |
| PYRE | 100 | 10 | 100 | 10 | 10 | 30 | >100 | 100 | 10 |
| HELM T | 100 | 10 | 100 | 10 | 10 | 30 | 100 | 30 | 10 |
| SEPT N | 100 | 10 | 100 | 10 | 10 | 30 | 100 | 30 | 30 |
| RHIZ C | 100 | 30 | 100 | 30 | 30 | 100 | >100 | 100 | 100 |
| SEPT T | 100 | | | | | >100 | >100 | | |

TABLE (V)

Minimal inhibitory dose in ppm

| | Compound n° | | | | | | | | | |
|---|---|---|---|---|---|---|---|---|---|---|
| Fungus | 28 | 29 | 30 | 31 | 32 | 33 | 34 | 35 | 36 | 37 |
| BOT | 1000 | 330 | | | | | | 1000 | | 1000 |
| ERYG | 110 | 110 | 110 | 330 | 110 | 110 | 330 | 110 | 110 | 1000 |
| PUCR | 110 | 110 | 110 | 330 | 110 | 110 | >1000 | 110 | >1000 | 1000 |
| PLA | 100 | | | 1000 | 330 | 1000 | 1000 | >1000 | >1000 | >1000 |
| PIR | 1000 | 1000 | | 1000 | | >1000 | | 110 | 1000 | |
| CBET | 1000 | 110 | | 1000 | 330 | 1000 | 1000 | 330 | 1000 | 1000 |
| PUCS | ≦250 | ≦250 | ≦250 | | | | | | | |
| ERYC | 125 | 125 | | | | | | | | |

| | Compound n° | | | | | | | | |
|---|---|---|---|---|---|---|---|---|---|
| Fungus | 38 | 39 | 40 | 41 | 42 | 43 | 44 | 49 | 50 |
| BOT | | >1000 | | | >1000 | 1000 | | 1000 | |
| ERYG | 1000 | 330 | 1000 | 1000 | 110 | 330 | >1000 | 330 | 1000 |
| PUCR | | 1000 | >1000 | 1000 | 1000 | 1000 | | >1000 | >1000 |
| PLA | | >1000 | >1000 | | >1000 | | | | >1000 |
| PIR | | | | | | | | | |
| CBET | >1000 | 330 | 1000 | 330 | 330 | 330 | 1000 | >1000 | |
| PUCS | | | | | | | | | |
| ERYC | | | | | | | | | |

TABLE (VI)

Minimal inhibitory dose in ppm
The figures in brackets show the degree of inhibition as a percentage at the stated dose

| | Compound n° | | | | | | | |
|---|---|---|---|---|---|---|---|---|
| Fungus | 45 | 29 | 12 | 35 | 9 | 28 | 47 | 48 |
| BOT | 30 | 10 | 100 | 10 | 30 | 10 | 100 (0) | 100 |
| FUS CULM | 100 | 30 | 100 | 30 | 11 | 30 | 100 | >100 (80) |
| FUS NIV | 100 | 30 | 100 | 100 | 33 | 30 | >100 | 30 |
| FUS ROS | 100 | 100 | >100 | 30 | 33 | 30 | >100 (80) | >100 (50) |
| CERC | 30 | ≦1 | 30 | 10 | 10 | 10 | 10 | 10 |
| HELM G | 30 | 10 | 100 | 10 | 11 | 10 | >100 | 30 |
| PYRE | 10 | 3 | 30 | 10 | 3,3 | 10 | >100 | 30 |
| HELM T | 3 | 3 | 10 | 10 | 3,3 | 3 | 100 | 10 |
| SEPT N | 3 | ≦1 | 30 | 10 | 3,3 | 3 | 100 | 10 |
| RHIZ C | 10 | ≦1 | 30 | 10 | 11 | 30 | >100 | 30 |

TABLE (VII)

| Fungus | Compound No. | Dose in g/Ha | percentage of spikes diseased | % of leaf surface diseased | Procedure for observing the results |
|---|---|---|---|---|---|
| PUCS | (control) | 0 | | 40 | 23 days after treatment; observation on the whole diseased plant at the 4 leaf stage |
| | 45 | 250 | | 17.5 | |
| | | 500 | | 16.3 | |
| | 29 | 250 | | 7.9 | |
| | | 500 | | 6.3 | |
| PUCS | (control) | 0 | | 82.3 | 14 days after treatment; observation on the |
| | 45 | 125 | | 3.4 | |
| | 29 | 125 | | 1.2 | 3rd leaf |
| PUCS | (control) | 0 | | 25.9 | 15 days after 1st treatment |
| | 45 | 125 | | 6.7 | observation on |
| | 29 | 125 | | 3.5 | the 1st leaf |
| ERYG | (control) | 0 | | 25.9 | 14 days after treatment; observation on |
| | 45 | 250 | | 4.7 | |
| | 29 | 250 | | 1.0 | the 3rd leaf |
| PUCS | (control) | 0 | 100 | 47.7 | 22 days after second treatment for the spikes; 7 days after 2nd treatment for verification on the 2nd leaf |
| | 12 | 125 | 88 | 5.8 | |
| | 28 | 125 | 64 | 0.8 | |
| ERYG | (control) | 0 | | 10.3 | 20 days after second treatment, verification on the 1st leaf |
| | 12 | 125 | | 0.9 | |
| | 28 | 125 | | 0.1 | |
| PUCS | (control) | 0 | 96 | | 24 days after the treatment |
| | 45 | 125 | 74 | | |
| | | 250 | 74 | | |
| | 29 | 125 | 54 | | |
| | | 250 | 46 | | |
| | 12 | 125 | 91 | | |
| | | 250 | 87 | | |
| | 28 | 125 | 39 | | |
| | | 250 | 46 percentage | | |

TABLE (VII)-continued

| Fungus | Compound No. | Dose in g/Ha | percentage of spikes diseased of stems diseased | % of leaf surface diseased | Procedure for observing the results |
|---|---|---|---|---|---|
| CERC | (control) | 0 | 93 | | 56 days after treatment; verification on the main stem |
| | 45 | 500 | 96 | | |
| | | 1000 | 90 | | |
| | 29 | 500 | 82 | | |
| | | 1000 | 72 | | |
| | 12 | 500 | 93 | | |
| | | 1000 | 85 | | |
| | 28 | 500 | 82 | | |
| | | 1000 | 63 | | |

II.

The objectives of the invention are also obtained by products having the following formula:

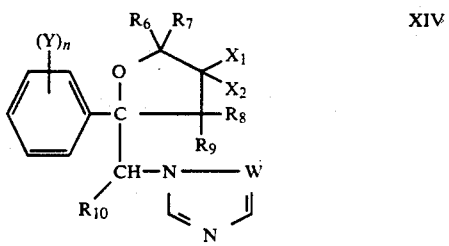

XIV in which

Y is a halogen atom or a cyano or nitro group, or an optionally halogenated alkyl or alkoxy group, n is a positive integer or zero, less than 6, it being possible for the groups Y to be identical or different when n is greater than 1, W represents a trivalent group consisting of either a =CH— group or a nitrogen atom =N—, $R_6$ to $R_{10}$, which may be identical or different, represent the hydrogen atom or a lower alkyl, lower cycloalkyl, aryl (especially phenyl), aralkyl (especially benzyl), lower alkoxy, lower alkanoyl or aroyl (especially benzoyl) radical, it being possible for these different radicals to be optionally substituted-(for example, with one or more atoms or radicals such as halogen atoms, and lower alkoxy radicals), $X_1$, $X_2$, which may be identical or different, represent the hydrogen atom, a halogen atom, a lower alkyl radical, a lower cycloalkyl radical, an aryl (especially phenyl) or aralkyl (especially benzyl) radical, it being possible for these different radicals to be optionally substituted in a similar way to the groups $R_6$ to $R_{10}$, a Q—$R_{11}$ group in which Q represents O or S, and $R_{11}$ represents the hydrogen atom or a lower alkyl radical, a lower cycloalkyl, aryl (especially phenyl), aralkyl (especially benzyl), acyl or thioacyl (especially acetyl, thioacetyl, propionyl, thiopropionyl), alkyloxythioyl, aryloxythioyl or aralkyloxythioyl (the term thioyl corresponds to C=S (S)) radical, it being possible for these radicals to be substituted in a similar way to the groups $R_6$ to $R_{10}$ and to have identical or different meanings when $X_1$ and $X_2$ each correspond to $OR_{11}$ or $SR_{11}$, a group of formula —Q—$R_{12}$Q where Q has the same meaning as before and in which $R_{12}$ is a divalent hydrocarbon radical, containing from 2 to 6 carbon atoms, it being possible for one of these carbon atoms to be replaced by an oxygen or nitrogen atom, the said single divalent radical itself being optionally substituted (for example, with one or more halogen atoms or lower alkyl, lower alkoxy or hydroxy radicals), an —$NR_{13}R_{14}$ group in which $R_{13}$ and $R_{14}$, which may be identical or different, represent the hydrogen atom or a lower alkyl radical, a lower cycloalkyl, aryl (especially phenyl) or aralkyl (especially benzyl) radical, it being possible for these different radicals to be optionally substituted in a similar way to the groups $R_6$ to $R_{10}$, or alternatively $R_{13}$ and $R_{14}$ may together form a single divalent hydrocarbon radical, containing from 3 to 6 carbon atoms, it being possible for one of these carbon atoms to be replaced by an oxygen, sulphur or nitrogen atom, the said single divalent radical itself being optionally substituted (for example with one or more halogen atoms or optionally halogenated lower alkyl or lower alkoxy radicals or a hydroxy radical), an =N—$R_{15}$ group in which $R_{15}$ corresponds to a lower alkyl radical, a lower cycloalkyl, aryl (especially phenyl) or aralkyl (especially benzyl) radical, to a group of formula $OR_{16}$ in which $R_{16}$ is an alkyl or an aralkyl or aryloxy radical, it being possible for these radicals to be substituted in a similar way to the groups $R_6$ to $R_{10}$, or hydroxy, an $N_3$ group, subject to the condition that $X_2$ is different from $N_3$, $X_1$ and $X_2$ may together form =O or =S, subject to the general condition that if $X_1$ is chosen from the list consisting of hydrogen, a lower alkyl radical, a lower cycloalkyl radical, an aryl radical or an aralkyl radical, $X_2$ cannot correspond to any one of the meanings on the same list.

The invention also relates to the salified forms of the compounds according to the invention. The salified forms are the forms which are acceptable in agriculture among which there may be mentioned the hydrochloride, sulphate, oxalate, nitrate or arylsulphonate and the addition complexes of these compounds with metal salts, and especially iron, chromium, copper, manganese, zinc, cobalt, tin, magnesium and aluminum salts.

By way of example, zinc complexes may be obtained by reacting the compound of formula XIV with zinc chloride.

Within the meaning of the present text, it is understood that the adjective lower, when it qualifies an organic radical, means that this radical contains no more than six carbon atoms. This radical may be straight-chain or branched.

In order to avoid all ambiguity, the term "compounds" will be used to denote those contained in formula XIV. In contrast, the compounds which may, if appropriate, be used as intermediates in the preparation processes will always be denoted by the said periphrasis.

The applicant wishes to emphasize that the plates appended should in no way be considered as drawings, but as forming an integral part of the description of the invention.

The compounds of formula XIV and the compounds which may, if appropriate, be used as intermediates in the preparation processes, and which will be defined at the time of describing these processes, may exist in one or more isomeric forms depending on the number of asymmetric centres in the molecule. Therefore, the invention relates to all the optical isomers as well as their racemic mixtures and the corresponding diastereoisomers. The separation of the diastereoisomers and/or the optical isomers may be carried out according to methods known per se.

For the purpose of fungicidal applications, it has been found that the invention related preferably to the compounds of formula XIV in which Y is a halogen and $n=1$, 2 or 3.

It has also been found that it was preferable to use the compounds of formula XIV in which $n=1$ or 2, and Y is a halogen atom placed in the ortho and/or para position.

Preferably also, $n=2$ and Y is a halogen atom, advantageously chlorine placed in the ortho and the para positions.

Taking into account the restrictions defined above, considered separately or in combination, it has been found that, by virtue of the fungicidal properties, it was preferable to use the compounds of formula XV in which $R_6$ to $R_{10}$, Y, n, $X_1$ and W have the same meaning as in formula XIV and Hal corresponds to a halogen atom, or alternatively the compounds of formula XVI in which $R_6$ to $R_{10}$, Y, n, $X_1$, W and $QR_{11}$ have the same meaning as in formula XIV except that $X_1$ is other than Hal.

The preferred compounds of formula XV are those in which the $R_6$ to $R_{10}$ groups correspond to a hydrogen atom or to a lower cycloalkyl or alkyl group and/or Hal corresponds to a bromine or chlorine atom.

The preferred compounds of formula XVI are those of which the $R_6$ to $R_{10}$ groups correspond to a hydrogen atom, or to a lower cycloalkyl or alkyl group, where $X_1$ corresponds to a hydrogen atom or lower cycloalkyl or alkyl group, and where $R_{11}$ corresponds to an optionally substituted cycloalkyl or alkyl group.

The present invention also relates to the processes for the preparation of the compounds according to the invention.

In the case where the $X_2$ group corresponds to a halogen atom (compound of formula XV), a preparation process consists of the following stages:

Stage a) A halo ketone of formula XVa obtained by a known process, in which Y, n and $R_{10}$ have the same meaning as given for the compounds of formula XIV and Z corresponds to a halogen atom, is reacted with an organometallic compound of formula XVb, in which $R_6$ to $R_9$ and $X_1$ have the same meaning as above and M corresponds to an alkali metal or a magnesium-containing group (Mg Hal) or a zinc-containing group (Zn Hal) for example, in a solvent, preferably chosen from ethers such as diethyl ether or tetrahydrofuran, aliphatic, alicyclic or aromatic hydrocarbons such as hexane or toluene at a temperature chosen between $-50°$ C. and the reflux temperature of the solvent in question and in a molar ratio of XVa:XVb which is preferably of between 1.1 and 0.2. The reaction leads to the compound of formula XVc after neutralization of the reaction medium.

Stage b) The compound of formula XVc is then reacted with an unsubstituted triazole or imidazole in the presence of an organic or inorganic base, for example pyridine, triethylamine, sodium hydroxide, potassium hydroxide, carbonates and bicarbonates of alkali or alkaline earth metals, and in a suitable solvent such as, for example, alcohols, ketones, amides, nitriles or optionally halogenated aromatic hydrocarbons, at a temperature of between 80° and the reflux temperature of the solvent and in a molar ratio of XVc:imidazole or triazole which is preferably of between 1.1 and 0.2, which leads to the compound of formula XVd. The reaction generally passes through an epoxide intermediate of formula XVh which may, if appropriate, be isolated or prepared separately by methods known to the man skilled in the art.

Stage c) A molecule of halogen or of mixed halogen is added, preferably mole for mole, to the compound XVd in an inert solvent such as saturated or optionally halogenated aromatic hydrocarbons, which leads to the compound XVe.

Stage d) The compound XV is preferably obtained at ambient temperature by the cyclization of the compound XVe in the presence of an organic or inorganic base indicated in b in a molar ratio of compound XV:base which is preferably of between 1.1 and 0.66. The reaction may be carried out in a protic or aprotic solvent (water, alcohol, ketone, nitrile, ester, saturated or optionally halogenated aromatic hydrocarbon, dimethyl sulphoxide or amide such as dimethylformamide).

A second process for the preparation of the compounds where the $X_2$ group is a halogen consists in placing stage b) of grafting the imidazole or triazole ring after stage d), using the same procedure for the different stages. Thus, a halogen or halogen halide (mixed halogen) molecule is added to the compound XVc to give the compound XVf, the latter then being cyclized to give the compound XVg, which is then provided with a triazole or imidazole group to give the compound XV.

Other preparation processes may, of course, also be suitable

In the case where the $X_2$ group corresponds to $QR_{11}$, and $X_1$ is other than Hal (compounds of formula XVI), one preparation process consists in reacting a compound of formula XV with a heteroatomic nucleophile of formula $R_{11}$—Q—E, in which $R_{11}$ and Q have the same meaning as in formula XIV and E is a cation, for example an alkali or alkaline earth metal or a quaternary ammonium. The reaction is carried out in a suitable solvent in the presence of a base and, if appropriate, a phase transfer catalyst and at reaction temperatures which are generally of between $-30°$ and the reflux temperature of the solvent used and in a molar ratio XVI:$R_{11}$QE which is preferably of between 1.2 and 0.1.

Another process consists in reacting the compound XVg under the same conditions with the same heteroatomic nucleophile to obtain a compound XVIa to which the triazole or imidazole ring is then attached as described previously.

It is also possible to obtain the compounds in the formula of which $R_{11}$ is an optionally mono- or polyhalogenated lower alkyl group, by reacting the compounds XVI or XVIa in the formula of which $R_{11}$ corresponds to the hydrogen atom with an alkyl halide (mono- or polyhalogenated, if appropriate) in a molar ratio of XVI or XVIa:halide which is preferably of between 1.1 and 0.2, in the presence of an organic or inorganic base. If the starting compound was XVIa, a triazole or imidazole ring is then attached.

In the case where $X_2$ corresponds to a hydroxyl group (compounds of formula XVI in which Q corresponds to the oxygen atom and $R_6$ to the hydrogen atom), compounds of formula XVg or XV may also be reacted, if appropriate, in the presence of an inert organic solvent, at a temperature of between −30° and the reflux temperature of the solvent, with a hydroperoxide, hydroxide, oxide or superoxide of an alkali metal, alkaline earth metal or other metal, in a molar ratio which is preferably of between 1.1 and 0.2, and, in the case where compound XVg is the starting compound, an imidazole or triazole ring may then be attached.

In the case where $X_2$ corresponds to $N_3$, the compounds XVg or XV are reacted with an alkali metal or ammonium azide in a molar ratio which is preferably of between 1.1 and 0.2, preferably in an aprotic solvent, at a temperature of between −30° and the reflux temperature of the solvent, and, if XVg was the starting compound, the azide compound is then reacted with an imidazole or triazole ring. In the case where $X_2$ corresponds to an alkyloxy or aryloxy or aralkyoxythioyl group, the compounds XVg or XV are reacted with an alkali metal or ammonium xanthate.

In the case where $X_2$ corresponds to a hydroxyl group, the compounds XVc or XVd may also be reacted with a peroxide in order to obtain the epoxide compounds of formula XVIb for XVc, and XVIc for the compound XVd. These epoxides may then be hydrated to triols XVId and XVIe respectively in a way which is well known. The cyclization is carried out in the presence of a dehydrating agent such as hydrochloric, hydrobromic, sulphuric or sulphonic acids, if appropriate in a protic or aprotic solvent. This leads to compound XVIa in which $QR_{11}$ corresponds to OH to which a triazole or imidazole ring is then attached, or to compound XVI in the case of the compound XVIe. Optionally, if necessary, the alcohol group may be protected in a manner known per se for compounds XVId and XVIe.

In the case where $X_1$ and $X_2$ together correspond to an oxygen atom which is doubly bonded to tetrahydrofuran (compounds of formula XVII where $X_1$ corresponds to the oxygen atom), one process of preparation consists in operating from a compound of formula XVIa or XVI in which $QR_{11}$ corresponds to hydroxyl and $X_1$ to hydrogen, with a well-known oxidizing agent in order to obtain a compound XVII or XVIIa onto which an imidazole or triazole ring is grafted.

In order to obtain the thioketone group (compound of formula XVII where $X_1$ corresponds to the sulphur atom) thionation of the ketone group is carried out by reacting the compounds XVII or XVIIa, for example, with $H_2S$ or $P_2S_5$ in a molar ratio which is preferably of between 1.1 and 0.2, in the presence of an inert organic solvent (pyridine or hydrocarbon, for example) at a temperature of between 20° and the reflux temperature.

In the case where $X_1$ and $X_2$ simultaneously correspond to $QR_{11}$ (compound of formula XVIII) the compounds of formula (XVII) or (XVIIa) in which $X_1$ (or $X_2$) corresponds to an oxygen or sulphur atom which is doubly bonded to tetrahydrofuran are reacted with a compound of formula $HQR_{11}$ were Q corresponds to O or S in a molar ratio which is preferably of between 1.1 and 0.2, in the presence of an acid catalyst and in a suitable solvent, which may be the alcohol or thiol itself, or an inert solvent such as hydrocarbons or alcohols. If the starting compound was that of formula XVIIa, the compound of formula XVIIIa is obtained and an imidazole or triazole ring is then grafted onto the compound of formula XVIIIa.

In the case where $X_1$ and $X_2$ correspond to $Q—R_{12}—Q$ and $R_{12}$ constitutes a single divalent radical as defined previously, the compounds of formula (XVII) or (XVIIa) are reacted with a compound $HQ—R_{12}—QH$ under the same conditions as for the monohydric alcohols or the monothiols. If XVIIa was the starting compound, the compound XVIIIb is obtained, to which an imidazole or triazole is attached under the same conditions as before.

In the case where $X_2$ corresponds to $N—R_{13}R_{14}$, a preparation process consists in reacting a compound of formula XV or of formula XVg with an amine of formula $H—NR_{13}R_{14}$ in a molar ratio of between 1.1 and 0.2, if appropriate in the presence of another organic or inorganic base. This leads to the compound of formula XIX in the case where the starting compound was that of formula XV and to compound XIXa to which an imidazole or triazole ring is subsequently attached in the case where the starting compound was that of formula XVg.

In the case where $X_1$ (or $X_2$) corresponds to the $=N—R_{15}$ group (compound of formula XX), a compound of formula XVII or XVIIa is reacted with an amine of formula $R_{15}—NH_2$ or with one of its salts in a molar ratio which is preferably of between 1.1 and 0.2, in an inert organic solvent. In the case of the compound XVIIa, the compound XXa is obtained, to which an imidazole or triazole ring is then attached.

The compound of formula XX in which $R_{15}$ corresponds to a hydroxyl radical may also be reacted with an alkylating agent of formula $R_{16}D$ in which $R_{16}$ is an optionally substituted aralkyl or lower alkyl radical and in which D corresponds to a leaving halogen, sulphonium, ammonium, sulphonate or sulphate group, in the presence of an organic or inorganic base, in order to obtain the oxime substituted on the oxygen.

The subject of the invention is also the compounds which can be used, if appropriate, as intermediates in the preparation processes described above and of formula XV, XVc, XVd, XVe, XVf, XVg, XVh, XVI, XVIa, XVIb, XVIc, XVId, XVIe, XVII, XVIIa, XVIII, XVIIIa, XVIIIb, XIX, XIXa, XX and XXa in which $R_6$ to $R_{11}$, Y, W, n, $X_1$, $X_2$, P, Hal and Z have any one of the meanings mentioned in the preceding description.

The present invention also relates to the use of the compounds of formula XIV as fungicides.

The compound according to the invention may be used for the preventive as well as curative control of fungi, especially of the basidiomycetes, ascomycetes, adelomycetes or fungi imperfecti type, in particular the rusts, mildew, cercoosporella diseases, fusarium diseases, helminthosporium diseases, septoria diseases and rhizoctonia diseases or crops and of plants in general and, in particular, of cereals such as wheat, barley, rye oats and their hybrids and also rice and maize. The compounds according to the invention are active, in particular, against fungi, especially of the basidiomycetes, ascomycetes, adelomycetes or fungi imperfecti types such as *Botrytis cinerea, Erysiphe graminis, Puccinia recondita, Piricularia oryzae, Cercospora beticola, Puccinia striiformis, Erysiphe cichoracearum, Fusarium oxysporum* (melonis), *Pyrenophora avenae, Septoria tritici, Venturia inaequalis, Whetzelinia sclerotiorum, Monilia laxa, Mycosphaerella fijiensis, Marssonina panettoniana, Alternaria solani, Aspergillus niger, Cercospora arachidicola, Cladosporium herbarum, Helminthosporium oryzae, Penicillium expansum,* Pestalozzia sp, *Phialophora cinerescens, Phoma betae, Phoma foveata, Phoma lingam, Ustilago maydis, Verticillium dahliae, Ascochyta pisi, Guignardia bidwellii, Corticium rolfsii, Phomopsis*

*viticola, Sclerotinia sclerotiorum, Sclerotinia minor, Coryneum cardinale* and *Rhizoctonia solani.*

They are also and continue to be active against the following fungi: *Acrostalagmus koningi,* the Alternaria, the Colletotrichum, *Corticium rolfsii, Diplodia natalensis, Gaeumannomyces graminis, Gibberella fujikuroi, Hormodendron cladosporioides, Lentinus degener* or *tigrinus, Lenzites quercina, Memnoniella echinata, Myrothecium verrucaria, Paecylomyces varioti, Pellicularia sasakii, Phellinus megaloporus, Polystictus sanguineus, Poria vaporaria, Sclerotium rolfsii, Stachybotris atra,* the Stereum, Stilbum sp., *Trametes trabea, Trichoderma pseudokoningi* and *Trichothecium roseum.*

The compounds of the invention are of special interest because of their broad spectrum as regards cereal diseases (mildew, rust, eyespot, net blotch, leaf spot and foot rot). They are also of special interest because of their effectiveness against gray mould (Botrytis) and cercospora diseases and, because of this, they may be applied on crops as caried as grape vine, vegetable crops and tree crops and tropical crops such as peanut, banana, coffee, pecan nut and others.

In addition to the applications already described above, the products according to the invention additionally have an excellent biocidal activity with respect to many other kinds of microorganisms, among which there may be mentioned in a non-limiting way fungi such as those belonging to the genera:

Pullularia such as the species *P. pullulans,* Chaetomium such as the species *C. globosum,* Aspergillus such as the species *Aspergillus niger,* Coniophora such as the species *C. puteana.*

Owing to their biocidal activity, the products of the invention make it possible to control effectively microorganisms whose proliferation gives rise to numerous problems in the agricultural and industrial fields. To this end, they are particularly well suited for the protection of plants or of industrial products such as wood, leather, paints, paper, ropes, plastics and industrial water circuits.

They are particularly well suited for the protection of lignocellulose products and especially of wood, whether it is timber for furniture or construction, or timber which is exposed to bad weather such as timber for fencing, vine stakes or railway sleepers.

The compounds according to the invention, used on their own or in the form of compositions as defined above in the treatments of wood, are generally employed with organic solvents and may, if appropriate, be used in combination with one or more known biocidal products such as pentachlorophenol, metal salts, especially copper, manganese, cobalt, chromium or zinc salts derived from inorganic or carboxylic acids (heptanoic, octanoic or naphthenic acids); organic complexes or tin, mercaptobenzothiazole, insecticides such as pyrethroids or organochlorine compounds.

Finally, they have an excellent selectivity with respect to crops.

They are advantageously applied at doses of 0.005 to 5 kg/ha, and more especially 0.01 to 0.5 kg/ha.

In practical use, the compounds according to the invention are rarely used alone. Most often they form part of compositions. These compositions, which can be used for the protection of plants against fungal diseases, or in plant growth regulating compositions, contain as the active substance a compound according to the invention as described previously, in association with solid or liquid carriers which are acceptable in agriculture, and/or surfactants, also acceptable in agriculture. Conventional inert carriers and conventional surfactants can especially be used.

The term "carrier", in the present description, denotes a natural or synthetic organic or inorganic material, with which the active substance is combined in order to facilitate its application on the plant, on seeds or on the soil. Therefore, this carrier is generally inert and it must be acceptable in agriculture, especially on the treated plant. The carrier may be solid (clays, natural or synthetic silicates, silica, resins, waxes, solid fertilizers, etc.) or liquid (water, alcohols, ketones, petroleum fractions, aromatic or paraffinic hydrocarbons, chlorinated hydrocarbons, liquefied gases, etc.).

The surfactant may be an emulsifier, dispersant or wetting agent of ionic or non-ionic type. For example, there may be mentioned polyacrylic acid salts, lignosulphonic acid salts, phenolsulphonic or naphthalene-sulphonic acid salts, polycondensates of ethylene oxide with fatty alcohols or with fatty acids or with fatty amines, substituted phenols (especially alkylphenols or arylphenols), sulphosuccinic acid ester salts, taurine derivatives (especially alkyltaurates), phosphoric esters of alcohols or of polycondensates of ethylene oxdie with phenols. The presence of at least one surfactant is generally indispensable when the active substance and/or the inert carrier are insoluble in water and the vector agent for the application is water.

Therefore, for their application, the compounds of formula (XIV) are generally in the form of compositions; these compositions according to the invention are themselves in fairly diverse solid or liquid forms.

As solid forms of compositions, there may be mentioned powders for dusting or scattering (with a content of the compound of formula (XIV) reaching up to 100%) and pellets, especially those obtained by extrusion, by compacting, by impregnation of a granulated carrier, or by granulation starting from a powder (the content of the compound of formula (XIV) in these pellets being between 1 and 80% in these latter cases).

As liquid forms of compositions, or forms intended to constitute liquid compositions when applied, there may be mentioned solutions, especially water-soluble concentrates, emulsifiable concentrates, emulsions, flowables, aerosols, wettable powders (or powder for spraying) and pastes.

The emulsifiable or soluble concentrates most frequently contain 10 to 80% of active substance, whereas the emulsions or solutions ready for application contain, for their part, 0.01 to 20% of active substance.

These compositions may also contain any other type of ingredients such as, for example, protective colloids, adhesives, thickeners, thixotropic agents, penetrants, stabilizers, sequestering agents and the like, as well as other known active substances with pesticidal properties (especially insecticidal or fungicidal properties) or properties which promote plant growth (especially fertilizers) or plant growth regulating properties. More generally, the compounds according to the invention may be combined with all those solid or liquid additives which correspond to the usual techniques of formulation.

For example, in addition to the solvent, the emulsifiable concentrates may contain, when necessary, 2 to 20% of suitable additives such as the stabilizers, surfactants, penetrants, corrosion inhibitors, colouring agents or adhesives mentioned above.

In the case where the compounds according to the invention are used as fungicides, the doses to be used may vary within broad limits according, in particular, to the virulence of the fungi and the climatic conditions.

In general, compositions containing 0.5 to 5,000 ppm of active substance are very suitable; these values apply to the compositions ready for application. Ppm denotes "parts per million". The range from 0.5 to 5,000 ppm corresponds to a range from $5 \times 10^{-5}$ to 0.5% (percentages by weight).

As regards compositions which are suitable for storage and transportation, they more advantageously contain from 0.5 to 95% (by weight) of active substance.

Thus, the compositions for agricultural use according to the invention may contain the active substances according to the invention within very broad limits, ranging from $5.10^{-5}\%$ to 95% (by weight).

By way of example, the compositions of some concentrates are given below.

| Example F (formulation) 1: | |
|---|---|
| active substance | 400 g/l |
| alkali metal dodecylbenzenesulphonate | 24 g/l |
| 10:1 ethylene oxide/nonylphenol condensate | 16 g/l |
| cyclohexanone | 200 g/l |
| aromatic solvent | q.s. 1 liter |

According to another formula for an emulsifiable concentrate, the following are used:

| Example F2: | |
|---|---|
| active substance | 250 g |
| epoxide-treated vegetable oil | 25 g |
| mixture of alkylaryl sulphonate, polyglycol ether and fatty alcohols | 100 g |
| dimethylformamide | 50 g |
| xylene | 575 g |

From these concentrates, by dilution with water, it is possible to obtain emulsions of any desired concentration, which are especially suitable for application on leaves.

Flowables, which can also be applied by spraying, are prepared so as to obtain a stable fluid product which does not settle; they usually contain from 10 to 75% of active substance, from 0.5 to 15% of surfactants, from 0.1 to 10% of thixotropic agents and from 0 to 10% of suitable additives such as antifoams, corrosion inhibitors, stabilizers, penetrants and adhesives, and, as a carrier, water or an organic liquid in which the active substance is of low solubility or insoluble: some solid organic substances or inorganic salts may be dissolved in the carrier to assist in preventing sedimentation, or as anti-freezes for the water.

The wettable powders (or powder for spraying) are usually prepared so as to contain 20 to 95% of active substance, and they usually contain, in addition to the solid carrier, from 0 to 5% of a wetting agent, from 3 to 10% of a dispersant, and, when necessary, from 0 to 10% of one or more stabilizers and/or other additives such as penetrants, adhesives, or anti-caking agents, coloring agents, etc.

By way of example, various compositions of wettable powders are given below:

| Examples F3: | |
|---|---|
| active substance | 50% |
| calcium lignosulphonate (deflocculant) | 5% |
| isopropyl naphthalenesulphonate (anionic wetting agent) | 1% |
| anti-caking silica | 5% |
| kaolin (filler) | 39% |

Another composition of powder for spraying, at 70% strength, uses the following constituents:

| Example F4: | |
|---|---|
| active substance | 700 g |
| sodium dibutylnaphthalenesulphonate | 50 g |
| condensation product of naphthalenesulphonic acid, phenolsulphonic acid and formaldehyde in proportions 3:2:1 | 30 g |
| kaolin | 100 g |
| whitener | 120 g |

Another composition of powder for spraying, at 40% strength, uses the following constituents:

| Example F5: | |
|---|---|
| active substance | 400 g |
| sodium lignosulphonate | 50 g |
| sodium dibutylnaphthalene sulphonate | 10 g |
| silica | 540 g |

Another composition of powder for spraying, at 25% strength, uses the following constituents:

| Example F6: | |
|---|---|
| active substance | 250 g |
| calcium lignosulphonate | 45 g |
| mixture of whitening and hydroxyethyl cellulose in equal parts by weight | 19 g |
| sodium dibutylnaphthalenesulphonate | 15 g |
| silica | 195 g |
| whitener | 195 g |
| kaolin | 281 g |

Another composition of powder for spraying, at 25% strength, uses the following constituents:

| Example F7: | |
|---|---|
| active substance | 250 g |
| iscooctylphenoxy-polyoxyethylene-ethanol | 25 g |
| mixture of whitener and hydroxyethyl cellulose in equal parts by weight | 17 g |
| sodium aluminosilicate | 543 g |
| kieselguhr | 165 g |

Another composition of powder for spraying, at 10% strength, uses the following constituents:

| Example F8: | |
|---|---|
| active substance | 100 g |
| mixture of sodium salts of sulphates of saturated fatty acids | 30 g |
| condensation product of naphthalenesulphonic acid and formaldehyde | 50 g |
| kaolin | 820 g |

To obtain these powders for spraying or wettable powders, the active substances are intimately mixed in suitable mixers with the additional substances, and the mixtures are ground in mills or other suitable grinders. Powders for spraying are thereby obtained, the wettability and suspendibility of which are advantageous; they may be suspended in water at any desired concentration and these suspensions may be very advantageously used, especially for application on plant leaves.

Instead of the wettable powders, pastes can be produced. The conditions and means of production and use of these pastes are similar to those for wettable powders or powders for spraying.

As already stated, the dispersions and aqueous emulsions, for example the compositions obtained by diluting with water a wettable powder or an emulsifiable concentrate according to the invention, are included within the general scope of the present invention. The emulsions can be of the water-in-oil or oil-in-water type, and they may have a thick consistency like that of "mayonnaise".

Pellets intended for placing on the soil are usually prepared so as to be between 0.1 and 2 mm in size, and they may be manufactured by agglomeration or impregnation. In general, the pellets contain 0.5 to 25% of active substance and 0 to 10% of additives such as stabilizers, slow-release modification agents, binders and solvents.

According to an example of pellet composition, the following constituents are used:

| Example F9: | |
|---|---|
| active substance | 50 g |
| epichlorohydrin | 2.5 g |
| cetyl polyglycol ether | 2.5 g |
| polyethylene glycol | 35 g |
| kaolin (particle size: 0.3 to 0.8 mm) | 910 g |

In this particular case, the active substance is mixed with epichlorohydrin and dissolved in 60 g of acetone; polyethylene glycol and cetyl polyglycol ether are then added. The kaolin is wetted with the solution obtained and the acetone is then evaporated under vacuum. A micropellet of this type is advantageously used to control soil fungi.

The compounds of formula (XIV) may also be used in the form of powders for dusting; a composition containing 50 g of active substance and 950 g of talc can also be used; a composition containing 20 g of active substance, 10 g of finely divided silica and 970 g of talc may also be used; these constituents are mixed and ground, and the mixture is applied by dusting.

Examples 11 to 17 illustrate particular ways of preparing the compounds according to the invention as well as these compounds themselves. The nomenclature of the compounds has been given according to French standards, except that the numbering of the substituents has been placed before the substituents themselves.

EXAMPLE 11

Preparation of 1-[4-bromo-2-(2,4-dichlorophenyl) tetrahydrofuran-2-ylmethyl]-1H-1,2,4-triazole. Compound Nos. XIVa and XIVb Stage a) Preparation of 1-chloro-2-(2,4-dichlorophenyl) 4-penten-2-ol:

An organomagnesium derivative is prepared by adding a solution of allyl bromide (110 cc) in ethyl ether (700 cc) and tetrahydrofuran (200 cc) with magnesium (110 g), between 15° and 20° C., over three hours. The mixture is refluxed for 30 min and decanted, the organic phase is evaporated and the residue is washed with ether.

A solution of alpha,2,4-trichloroacetophenone (175 g) in tetrahydrofuran (250 g) at −30° C. is added and the mixture is neutralized with acetic acid. This is washed with water, dried over sodium sulphate, concentrated and then distilled under vacuum. A colourless oil is obtained (205 g). b.p. (3.10$^{-2}$mm Hg)=140–142° C.

Stage b) Preparation of 1-[2-(2,4-dichlorophenyl)-2-hydroxypenten-4-yl]-1H-1,2,4-triazole A mixture of the product obtained in stage a) (106 g), triazole (55 g) and potassium carbonate (160 g) is heated in dimethylformamide (600 cc) at 120° for four hours. The insoluble materials are filtered and washed with dimethylformamide, and the reaction mixture is concentrated under vacuum. The residue, dissolved in methylene chloride, is washed with water and then concentrated. The product is obtained by crystallization in ethyl acetate after dilution with heptane. A pale pink solid, m.p. 101°, is isolated (97 g).

Stage c) Preparation of the Compound Nos. 51a and 51b

The compound obtained in stage b (35 g) in chloroform (200 cc) is treated with bromine at 0°. After decolorizing, the solvent is evaporated and the residue redissolved in methanol. An aqueous solution of potassium hydroxide is then added until a basic pH is obtained. After evaporating the medium under vacuum, the residue is extracted with ethyl acetate, washed with water and concentrated. The oil obtained (40 g) consists of a mixture of two diastereoisomers in substantially equal proportions. Using silica column chromatography, the least polar isomer No. 51a: white crystals m.p. 83°, and then the most polar isomer No. 51b: white crystals m.p. 94°, are isolated in sequence. After recrystallization, 51a, m.p. 96° and 51b, m.p. 104°, are obtained.

EXAMPLE 12

Preparation of 1-[2-(2,4-dichlorophenyl)-4-hydroxytetrahydrofuran-2-ylmethyl]-1H-1,2,4-triazole. Compound Nos. 52a and 52b The isomer (10 g) 51a of Example 11, which is the least polar isomer, dissolved in chlorobenzene (30 cc), is refluxed for 48 h, in the presence of sodium benzoate (20 g) in water (30 cc), and the phase transfer catalyst "ADOGEN 464" methyltrialkylammonium chloride (1 g).

After diluting with ether, the organic phase is washed with water and reduced under vacuum. The residue is then treated with methanol (100 cc) in the presence of potassium hydroxide (7 g) at reflux temperature for 3 hours. The mixture is cooled, diluted with water and extracted with ethyl acetate, and the product washed to neutrality and purified by chromatography, the crude product being obtained after concentration under vacuum. The alcohol 52a is isolated in the form of a white powder (2.8 g), m.p. 193°.

Operating in the same way, starting from the most polar isomer 51b obtained according to Example 11, the optically active alcohol 52b is obtained in the form of a white powder, m.p. 162° C.

EXAMPLE 13

Preparation of 1-[2-(2,4-dichlorphenyl)-4-ethoxytetrahydrofuran-2-ylmethyl]-1H-1,2,4-triazole. Compound Nos. 53a and 53b The alcohol 52a (2.2 g) dissolved in dimethylsulphoxide (12 cc) is treated, in sequence, with 80% strength sodium hydride (0.42 g) and then with ethyl iodide (1.15 cc). After 15 minutes, the medium is diluted with water and extracted with ethyl acetate. After washing with water, the solvent is evaporated and the residue is purified by silica column chromatography to obtain a colourless oil which is the isomer 53a which crystallizes on trituration with pentane m.p. 90°; in the same way, starting with 52b, the isomer 53b, which is a white powder, m.p. 63°, is obtained.

EXAMPLE 14

Preparation of
1-[2-(2,4-dichlorophenyl)-4-ethylthiotetrahydrofuran-2-ylmethyl]-1H-1,2,4-triazole. Compound Nos. 54a and 54b The bromide 51a (3.8 g) dissolved in dimethylsulphoxide (38 cc) containing water (2 cc) is treated with sodium hydrogen sulphide (2.8 g) for 2 hours. Powdered potassium hydroxide (3.3 g) is then added, followed by ethyl iodide (4 cc). After 10 minutes of stirring, the medium is diluted with water and extracted with ether. After drying and evaporation, the isomer 54a, which is a yellow oil (3.9 g), m.p. 88°, is obtained.

Operating in the same way, starting from 51b, 54b is obtained in the form of a pale yellow powder, m.p. 64°.

EXAMPLE 15

Preparation of
1[7-(2,4-dichlorophenyl)-1,4,6-trioxospiro[4.4]nonan-7-ylmethyl]-1H,1,2,4,-triazole. Compound No. 55

Stage a) Preparation of
1-chloro-2-(2,4-dichlorophenyl)-3,4,5-pentanetriol.

The chlorohydrin obtained in stage a) of Example 11 (91 g) is epoxidized in 1,2-dichloroethane (125 cc) in the presence of vanadyl acetylacetonate (5 g) and 70% strength tert-butyl peroxide (200 cc) by heating at the reflux temperature for 48 hours. The cooled medium is diluted with water, washed several times with a sodium bisulphite solution and then concentrated. The residue is then converted to triol by heating in water (200 cc) and dioxane (200 cc) in the presence of perchloric acid (5 cc) for 3 hours. After dilution with water, the medium is extracted with toluene (300 cc) and then concentrated.

Stage b) Preparation of
2-(2,4-dichlorophenyl)-2-chloromethyltetrahydrofuran-4-one The oily residue obtained in stage a) is then heated in toluene (100 cc) and butanol (200 cc) in the presence of paratoluenesulphonic acid (0.5 g), with the separation of the water formed. After evaporating the reaction medium, the residue is chromatographed on a silica column (40:60 ethyl acetate/heptane eluant) to obtain a colourless oil (14.5 g) corresponding to a mixture of alcohol diastereoisomers, namely 2-(2,4-dichlorophenyl)-4-hydroxy-2-chloromethyltetrahydrofuran.
This product is directly oxidized with chromic anhydride in acetic acid to obtain, after purification by silica column chromatography, furanone in the form of white crystals, m.p. 99° C.

Stage c) Preparation of
7-chloromethyl-7-(2,4-dichlorophenyl)-1,4,6-trioxaspiro[4.4]nonane.

The furanone obtained in stage b) (4.2 g), in toluene (50 cc), is heated at reflux temperature in the presence of ethylene glycol (6.5 cc) and p-toluenesulphonic acid (0.1 g), with the separation of the water formed, until the disappearance of the starting product.
The medium is washed with sodium hydroxide and then diluted with water, extracted with ether and concentrated. A white solid (5.1 g), m.p. 99°, is obtained.

Stage d) Preparation of Compound No. 55

The halide of stage c) (5 g) in dimethyl sulphoxide (20 cc) is heated to 170° in the presence of triazolyl sodium (2.75 g) for 6 hours. The medium is poured into water, extracted with ethyl acetate, concentrated and purified by silica column chromatography. After recrystallization in an ethyl acetate/heptane mixture, pale yellow crystals (3.6 g), m.p. 123°, are isolated.

EXAMPLE 16

Preparation of
1-[4-chloro-2-(2,4-dichlorophenyl)-tetrahydrofuran-2-ylmethyl]-1H-1,2,4,-triazole. Compound Nos. 56a and 56b

Stage a) Preparation of
2-(2,4-dichlorophenyl)-1,4,5-trichloro-2-pentanol.

The chlorohydrin obtained in stage a) of Example 11 dissolved in dichloromethane (150 cc) is treated with gaseous chlorine (13.4 g) at −15°. The medium is then treated with a 37% strength sodium bisulphite solution (15 cc), washed with water, dried and then evaporated. A crude product in the form of a colourless oil (49.7 g) containing approximately 70% of the desired product in the form of a mixture of two diastereoisomers is obtained.

Stage b) Preparation of
1-(2,4-dichlorophenyl)-1-(2,3-dichloro-1-propanyl)oxirane A first method consists in dissolving the crude chlorohydrin (10.3 g) obtained in stage a) above in methanol (30 cc) and treating it with a solution of methanolic potassium hydroxide (12 cc) at a concentration of $2.55 \times 10^3$ moles/liter, at ambient temperature. The precipitate is filtered and the methanolic solution is evaporated under vacuum. The residue is purified by silica column chromatography. A colourless oil is obtained (7.4 g).

A second method consists in dissolving the chlorohydrin (19.9 g) obtained in stage a of Example 11 in methanol (75 cc), and treating it with a potassium hydroxide (4.9 g) solution in methanol (20 cc) at ambient temperature. After the filtration of the insoluble material and evaporation, epoxide (17.1 g) is obtained in the form of a yellow oil. This epoxide is treated with chlorine until the yellow colour (10.1 g) persists at −15° C. The medium is then washed with a sodium bisulphite solution followed by water, and then evaporated under vacuum. A yellow oil (20.8 g) consisting of a mixture of two diastereoisomers in a ratio of 45:55 is obtained.

Stage c) Preparation of
1-[4-chloro-2-(2,4-dichlorophenyl) tetrahydrofuran-2-ylmethyl]-1H-1,2,4-triazole The epoxide obtained in stage b) (61.7 g) in 1-butanol (0.5 liter) is heated at 90° for 6 hours in the presence of triazolyl sodium (18.6 g). The inorganic precipitate is filtered and the butanol is evaporated. The residue is purified by silica column chromatography (48% ethyl acetate:48% heptane:4% methanol eluant) to obtain, in sequence, the first diastereoisomer 57a, m.p., 113°, and then the second diastereoisomer 57b, m.p. 97°.

EXAMPLE 17

The compounds which follow, which have been combined in a table below for ease of reading, were prepared in the same way. These are compounds the common structure of which corresponds to formula XXI. Therefore, only the meaning of the groups $X_1$ and $X_2$ and the m.p. (the indices a and b indicate the isomerism) are given in the table.

| No. | $X_1$ | $X_2$ | m.p. |
|---|---|---|---|
| 57a | H | $SCH_3$ | 96 |
| 57b | $SCH_3$ | H | oil |
| 58a | H | $SC_3H_7$ | 110 |
| 58b | $SC_3H_7$ | H | oil |

Examples 18 to 22 illustrate the fungicidal applications of the compounds according to the invention.

In these examples, the sprayings of solutions or suspensions of active substances are carried out under conditions such that the spraying of a solution or suspension of concentration equal to 1 g/liter corresponds on average to the application of approximately 2 micrograms of active substance per $cm^2$ of leaf area of the plant.

Under the conditions of Examples 19 to 22, the compounds illustrated showed to phytotoxicity.

In these examples, a product is regarded as providing complete protection against a fungal disease when the protection is at least 95%; the protection is regarded as good when it is at least 80% (but less than 95%), as fairly good when it is at least 70% (but less than 80%) and as average when it is at least 50% (but less than 70%).

In the present account, the percentages are, except where otherwise indicated and except those relating to yields, percentages by weight. In the case where the percentages are expressed relative to the stoichiometry, these are major percentages. As regards concentrations, some of these are expressed in ppm (part per million) which corresponds to mg/liter.

EXAMPLE 18

Test in vivo on *Botrytis cinerea* on Tomato

An aqueous emulsion of the active substance to be tested, having the following composition, is prepared by fine grinding:
  active substance under test: 60 mg
  Tween 80 (surfactant consisting of an oleate of a polycondensate of ethylene oxide with a sorbitan derivative) diluted to 10% strength in water: 0.3 cc
  the volume is made up to 60 cc with water.

This aqueous emulsion is then diluted with water to obtain the desired concentration.

30- to 40-day-old, greenhouse-cultivated tomatoes (variety Marmande) are treated by spraying with aqueous emulsions (called slurries) as defined above and at various concentrations of the compound to be tested. The trial is replicated twice with each concentration.

After 24 or 48 hours, the leaves are cut and placed in 2 Petri dishes (diameter 14 cm) the base of which has previously been provided with a disc of moist filter paper (5 sheets per dish).

The inoculum is then applied by means of a syringe by depositing drops (3 drops per leaflet) of a spore suspension. This suspension of *Botrytis cinerea* spores was obtained from a 15-day-old culture, which was then suspended in a nutrient solution (100,00 units/cc).

Verification is carried out 3 and 6 days after the inoculation by comparison with an untreated control.

Under these conditions, at a dose of 1 g/liter, a good or total protection is observed with compounds 51a, 51b, 56a, 56b, 57a and 58a.

EXAMPLE 19

Test in vivo on *Erysiphe graminis* on Barley (Barley Mildew)

Barley, in pots, sown in plain soil, is treated at the 10 cm height stage by spraying with an aqueous emulsion (called slurry) at the concentration indicated below. The trial is replicated twice. After 24 hours, the barley plants are dusted with *Erysiphe graminis* spores, the dusting being carried out using diseased plants.

Readings are taken 8 to 14 days after inoculation.

Under these conditions, the following results are observed: at a dose of 1 g/liter, good or total protection with 51a, 53a, 53b, 54a, 55, 56a, 56b, 57a, 58a, 58b and 51a+51b.

EXAMPLE 20

Test in vivo on "*Puccinia recondita*" Responsible for Wheat Rust

Wheat, in pots, sown in plain soil, is treated at the 10 cm height stage by spraying with aqueous emulsions (called slurries) of the same composition as that described in Example 18 and at various concentrations of the compound to be tested. The trial is replicated twice at each concentration.

After 24 hours, an aqueous suspension of spores (50,000 sp/cc) is sprayed onto the wheat; this suspension was obtained from contaminated plants. The wheat is then placed for 48 hours in an incubation cell at approximately 18° C. and at 100% relative humidity.

After these 2 days, the relative humidity is lowered to 60%. The condition of the plants is verified between the 11th and the 15th days, after inoculation, by comparison with the untreated control.

At a dose of 1 g/liter, good or total protection with compounds 51a, 51b, 53a, 53b, 54a, 54b, 55, 56a, 56b, 57a, 58a, 58b, 51a+51b and 54a+54b.

EXAMPLE 21

Test in vivo on "*Piricularia oryzae*" Responsible for Rice Blast

Rice, in pots, sown in a 50:50 mixture of enriched peat and pozzolana, is treated at the 10 cm height stage by spraying with an aqueous emulsion (called slurry) defined above at the concentration indicated below. The trial is repeated twice. After 48 hours, treatment is carried out by applying on the leaves a suspension of spores obtained in pure culture.

Verification is carried out 8 days after inoculation. Under these conditions, the following results are observed: at a dose of 1 g/liter, good or total protection with compounds 51a, 51b, 53a, 53b, 56a, 56b, 57a, 57b, 58a, 58b and 51a+51b.

EXAMPLE 22

Test in vitro on Seed Fungi and Soil Fungi

The action of the compounds according to the invention is studied on the following fungi responsible for diseases of cereals and other plants:
1) *Pyrenophorae avenae*
2) *Septoria nodorum*
3) *Helminthosporium teres*
4) *Fusarium roseum*

5) *Fusarium nivale*
6) *Fusarium culmorum*
7) *Rhizoctonia cerealis*
8) *Septoria tritici*
9) *Botrytis cinerea* sensitive to carbendazime and to cyclic imides
10) *Botrytis cinerea* resistant to carbendazime and to cyclic imides
11) *Pseudocercosporella herpotrichoides*
12) *Fusarium oxysporum* F. sp melonis
13) *Rhizoctonia solani*
14) *Helminthosporium gramineum*

The numbers which appear before the names will be used to represent these fungi in Table (II).

For each trial, the procedure is as follows: a nutrient medium consisting of potato, glucose and agar (PDA medium) is introduced supercooled into a series of Petri dishes (20 cc per dish) after sterilizing in an autoclave at 120° C.

In the course of filling the dishes, an acetone solution of the active substance is injected into the supercooled medium, to obtain the desired final concentration.

Petri dishes similar to the above, into which are poured similar quantities of a nutrient medium which does not contain the active substance, are taken as control.

After 24 or 48 h each dish is seeded by depositing a fragment of mycelium originating from a previous culture of the same fungus.

The dishes are stored for 2 to 10 days (depending on the fungus being tested) at 22° C., and the growth of the fungus in the dishes containing the active substance to be tested is compared with that of the same fungus in the dish used as the control.

For each compound tested, the degree of inhibition of the fungus considered at a dose of 30 ppm, is thus determined.

| Compound No. | Fungi | | | | | | |
|---|---|---|---|---|---|---|---|
| | 1 | 2 | 3 | 4 | 5 | 6 | 7 |
| 51a | 100 | 90 | 100 | 95 | 100 | 100 | 95 |
| 51b | 100 | 90 | 100 | 100 | 100 | 100 | 90 |
| 51b + 51b (50/50) | 100 | 100 | 100 | 95 | 100 | 100 | 90 |
| 53a | 90 | 90 | 90 | 80 | 80 | 80 | 90 |
| 53b | 80 | 90 | 80 | 0 | 0 | 0 | 80 |
| 54a | 80 | 95 | 50 | 0 | 0 | 0 | 50 |
| 54b | 95 | 90 | 95 | 0 | 0 | 0 | 50 |
| 55 | 100 | 50 | 95 | 80 | 50 | 50 | 0 |
| 54a + 54b | 95 | 95 | 95 | 0 | 0 | 0 | 50 |
| 56a | 95 | 95 | 100 | 95 | 100 | 100 | 90 |
| 56b | 95 | 90 | 100 | 90 | 95 | 100 | 90 |
| 57a | 100 | 90 | 95 | 80 | 80 | 90 | 80 |
| 57b | 95 | 80 | 95 | 80 | 50 | 100 | 80 |
| 58a | 95 | 90 | 95 | 80 | 80 | 90 | 80 |
| 58b | 90 | 80 | 95 | 80 | 80 | 80 | 80 |

| Compound No. | Fungi | | | | | | |
|---|---|---|---|---|---|---|---|
| | 8 | 9 | 10 | 11 | 12 | 13 | 14 |
| 51a | 100 | 100 | 90 | 100 | 100 | 80 | 100 |
| 51b | 0 | 100 | 95 | 100 | 100 | 80 | 100 |
| 51a + 51b (50/50) | 0 | 100 | 95 | 100 | 100 | 90 | 95 |
| 53a | 80 | 100 | 95 | 90 | 80 | 80 | 90 |
| 53b | 0 | 95 | 90 | 95 | 0 | 0 | 80 |
| 54a | 0 | 100 | 95 | 100 | 50 | 80 | 50 |
| 54b | 0 | 95 | 95 | 90 | 0 | 50 | 50 |
| 55 | 0 | 0 | 0 | 90 | 50 | 100 | 90 |
| 54a + 54b | 0 | 100 | 95 | 95 | 0 | 80 | 80 |
| 56a | 0 | 100 | 100 | 100 | 100 | 80 | 100 |
| 56b | 0 | 100 | 95 | 100 | 80 | 80 | 100 |
| 57a | 0 | 100 | 95 | 90 | 80 | 80 | 95 |
| 57b | 0 | 90 | 80 | 80 | 80 | 80 | 95 |
| 58a | 0 | 100 | 95 | 90 | 80 | 80 | 100 |
| 58b | 0 | 25 | 80 | 80 | 80 | 80 | 90 |

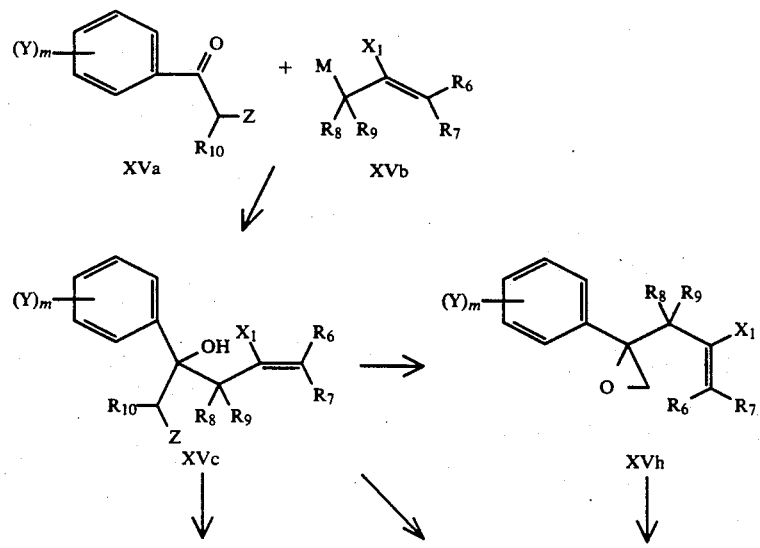

-continued
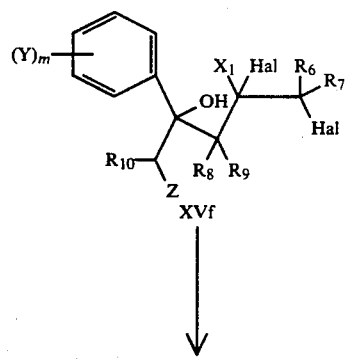
XVf
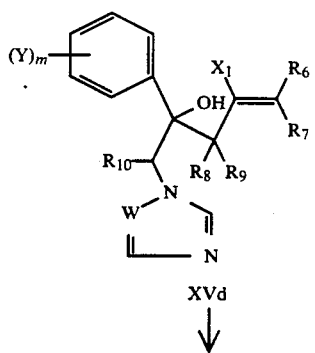
XVd
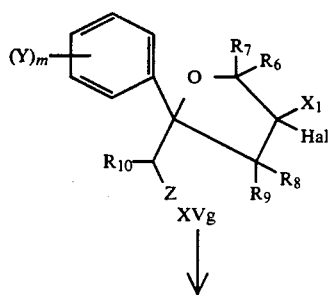
XVg
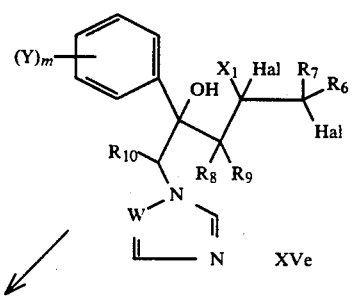
XVe
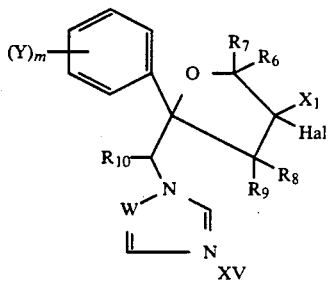
XV
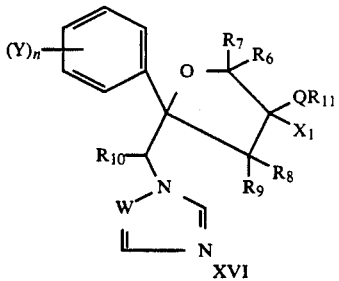
XVI
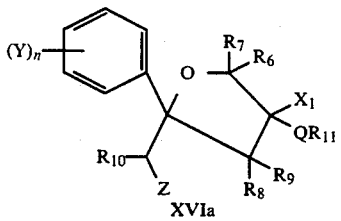
XVIa
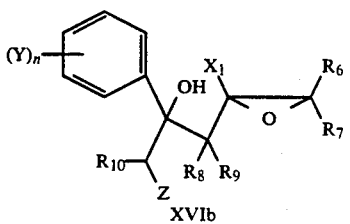
XVIb
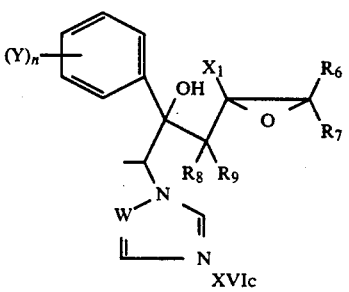
XVIc -continued
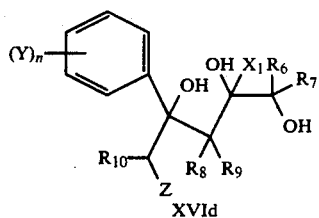
XVId
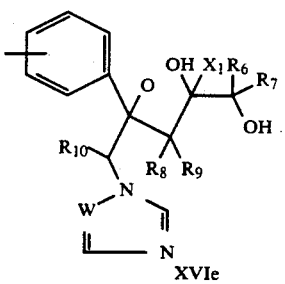
XVIe
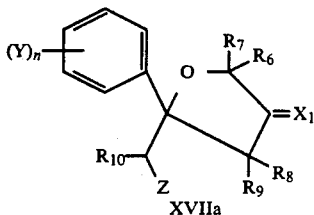
XVIIa
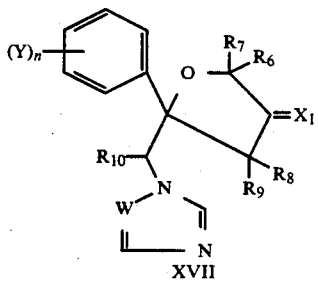
XVII
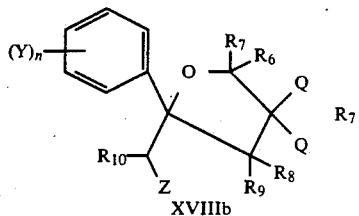
XVIIIb
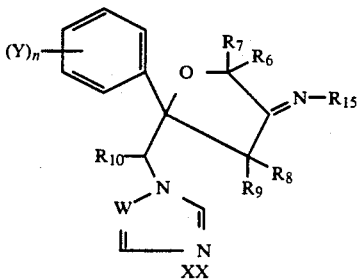
XX
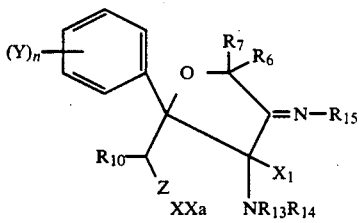
XXa
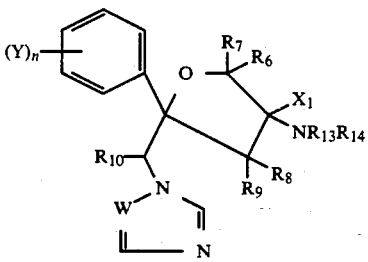
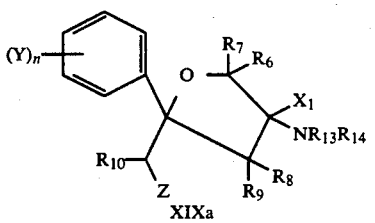
XIXa
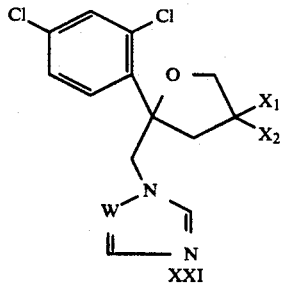
XXI
We claim:
1. The compound 1-[4-bromo-2-(2,4-dichlorophenyl) tetrahydrofuran-2-ylmethyl]-1H-1,2,4-triazole.
* * * * *

UNITED STATES PATENT AND TRADEMARK OFFICE
CERTIFICATE OF CORRECTION

Page 1 of 3

PATENT NO. : 5,210,198
DATED : May 11, 1993
INVENTOR(S) : Jean-Claude Debourge, et. al.

It is certified that error appears in the above-indentified patent and that said Letters Patent is hereby corrected as shown below:

Column 2, line 16, "W" should read as --N--.
Column 7, line 33, "(XIII)" should read as --(XII)--.
Column 16, line 53, before "delta" insert --(--.

Column 20, line 47: "$CH_2H_5$-" should read as --$C_2H_5$- --

Column 20, line 47: "/4,64" should read as --/4,84--

Column 24, lines 2-12, Column 42 of Table IV:

" 30 " should read as -- 30 --

| | |
|---|---|
| | >100 |
| >100 | 100 |
| 100 | 100 |
| 100 | 100 |
| 100 | 100 |
| 100 | 100 |
| 100 | 100 |
| 10 | 10 |
| 10 | 10 |
| 10 | 10 |
| 30 | 30 |

Column 25, line 46: after "substituted" delete -- - --

UNITED STATES PATENT AND TRADEMARK OFFICE
CERTIFICATE OF CORRECTION

PATENT NO. : 5,210,198
DATED : May 11, 1993
INVENTOR(S) : Jean-Claude Debourge, et al.

It is certified that error appears in the above-indentified patent and that said Letters Patent is hereby corrected as shown below:

Column 45, line 25: insert the following

-- 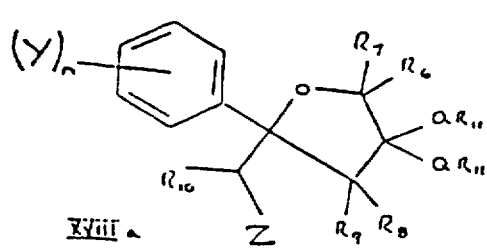 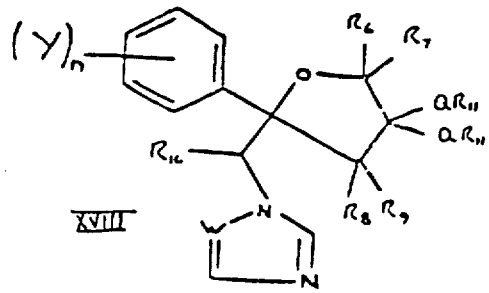 --.

UNITED STATES PATENT AND TRADEMARK OFFICE
CERTIFICATE OF CORRECTION

Page 3 of 3

PATENT NO. : 5,210,198
DATED : May 11, 1993
INVENTOR(S) : Jean-Claude Debourge, et. al.

It is certified that error appears in the above-indentified patent and that said Letters Patent is hereby corrected as shown below:

Column 45, line 30: in formula XVIIIb " $\underset{R_7}{\overset{Q}{Q}}$ " should read as 

Signed and Sealed this

Twenty-second Day of November, 1994

*Attest:*

BRUCE LEHMAN

*Attesting Officer*   Commissioner of Patents and Trademarks